United States Patent
Ueya

(10) Patent No.: US 11,125,747 B2
(45) Date of Patent: Sep. 21, 2021

(54) SOLID PHASE CARRIER, LIGAND-BOUND SOLID PHASE CARRIER, METHOD FOR DETECTING OR SEPARATING TARGET SUBSTANCE, AND METHOD FOR PRODUCING SOLID PHASE CARRIER

(71) Applicants: JSR CORPORATION, Minato-ku (JP); JSR Life Sciences Corporation, Minato-ku (JP)

(72) Inventor: Yuuichi Ueya, Minato-ku (JP)

(73) Assignees: JSR CORPORATION, Minato-ku (JP); JSR Life Sciences Corporation, Minato-ku (JP)

( * ) Notice: Subject to any disclaimer, the term of this patent is extended or adjusted under 35 U.S.C. 154(b) by 185 days.

(21) Appl. No.: 15/509,684

(22) PCT Filed: Sep. 7, 2015

(86) PCT No.: PCT/JP2015/075333
§ 371 (c)(1),
(2) Date: Mar. 8, 2017

(87) PCT Pub. No.: WO2016/039293
PCT Pub. Date: Mar. 17, 2016

(65) Prior Publication Data
US 2017/0292947 A1    Oct. 12, 2017

(30) Foreign Application Priority Data
Sep. 8, 2014   (JP) .............. JP2014-182069

(51) Int. Cl.
*G01N 33/543*    (2006.01)
*G01N 33/547*    (2006.01)
(Continued)

(52) U.S. Cl.
CPC ......... *G01N 33/547* (2013.01); *C08F 257/02* (2013.01); *C08F 293/00* (2013.01);
(Continued)

(58) Field of Classification Search
CPC .. C08F 257/02; C08F 293/00; C08F 293/005; C08F 220/14; C08F 2438/01;
(Continued)

(56) References Cited

U.S. PATENT DOCUMENTS

| | | |
|---|---|---|
| 2008/0139399 A1 | 6/2008 | Fonnum et al. |
| 2009/0061533 A1 | 3/2009 | Minami et al. |
| 2017/0146528 A1 | 5/2017 | Ueya |

FOREIGN PATENT DOCUMENTS

| | | |
|---|---|---|
| CN | 101341408 A | 1/2009 |
| EP | 3 115 384 A1 | 1/2017 |

(Continued)

OTHER PUBLICATIONS

Coessens et al. Fundamentals of atom transfer radical polymerization. J. Chemical Education 2010, vol. 87, No. 9, pp. 916-919. (Year: 2010).*

(Continued)

*Primary Examiner* — Shafiqul Haq
(74) *Attorney, Agent, or Firm* — Oblon, McClelland, Maier & Neustadt, L.L.P.

(57) ABSTRACT

Provided is a solid phase carrier which has high water dispersibility, allows facilitated binding of a ligand to a reactive functional group, and exhibits suppressed non-specific adsorption, and with which, in the case of using the solid phase carrier by having a ligand bound thereto, for example, detection of a target substance can be carried out with high sensitivity and low noise. Disclosed is a solid phase carrier having bound thereto a polymer including a structural unit represented by the following Formula (1) and a structural unit represented by the following Formula (2):

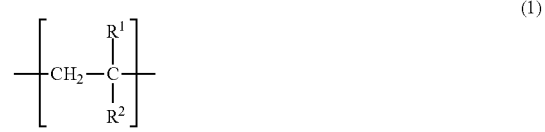

wherein in Formula (1),
$R^1$ represents a hydrogen atom or a methyl group; and
$R^2$ represents an organic group having a zwitterionic structure,

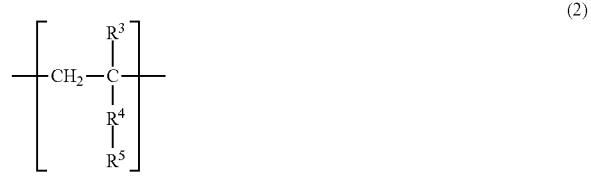

in Formula (2),
$R^3$ represents a hydrogen atom or a methyl group
$R^4$ represents —(C=O)—O—*, —(C=O)—NR$^6$—* (wherein $R^6$ represents a hydrogen atom or a methyl group; and the symbol * represents a position of bonding to $R^5$ in Formula (2)), or a phenylene group;
in a case in which $R^4$ represents —(C=O)—O—*, $R^5$ represents a hydrogen atom, or an organic group having a reactive functional group, and in a case in which $R^4$ represents —(C=O)—NR$^6$—* or a phenylene group, $R^5$ represents an organic group having a reactive functional group, provided that $R^5$ is not an organic group having a zwitterionic structure.

23 Claims, No Drawings

(51) Int. Cl.
  *C08F 293/00* (2006.01)
  *C08F 257/02* (2006.01)
  *C08L 43/02* (2006.01)
(52) U.S. Cl.
  CPC .......... *C08F 293/005* (2013.01); *C08L 43/02* (2013.01); *G01N 33/54326* (2013.01); *G01N 33/54393* (2013.01); *C08F 2438/01* (2013.01)
(58) Field of Classification Search
  CPC .......... G01N 33/547; G01N 33/54393; G01N 33/54326; C08L 43/02
  See application file for complete search history.

(56) References Cited

FOREIGN PATENT DOCUMENTS

| | | |
|---|---|---|
| JP | 2007-155623 A | 6/2007 |
| JP | 2009-69141 A | 4/2009 |
| JP | 2009-542862 A | 12/2009 |
| WO | 2008/003099 A1 | 1/2008 |
| WO | 2013/047527 A1 | 4/2013 |

OTHER PUBLICATIONS

Kuo et al. Surface modification with poly(sulfobetaine methacrylate-co-acrylic acid) to reduce fibrinogen adsorption, platelet adhesion, and plasma coagulation. Biomacromolecules 2011, vol. 12, pp. 4348-4356. (Year: 2011).*

Wu et al. Carboxybetaine, sulfobetaine, and cationic block copolymer coatings: a comparison of the surface properties and antibiofouling behaviour. J. Applied Polymer Science, 2011 vol. 124, pp. 2154-2170 (Year: 2011).*

Yang et al. Pursuing "zero" protein adsorption of poly(carboxybetaine) from undiluted blood serum and plasma. Langmuir 2009, vol. 25, No. 19, pp. 11911-11916. (Year: 2009).*

Philippova et al. Magnetic polymer beads: recent trends and developments in synthetic design and applications. European Polymer Journal 2011, vol. 47, pp. 542-559. (Year: 2011).*

Fristrup, Charlotte Juel. Polymers for pharmaceutical packaging and delivery systems. PhD Thesis, 2010, DTU Chemical Engineering, Department of Chemical and Biochemical Engineering, Technical University of Denmark, pp. 1-82. (Year: 2010).*

Zhang et al. Development of a stable dual functional coating with low non-specific protein adsorption and high sensitivity for new superparamagnetic nanospheres. Langmuir, 2011, vol. 27, pp. 13669-13674. (Year: 2011).*

Kostina et al. Non-fouling hydrogels of 2-hydroxyethyl methacrylate and zwitterionic carboxybetaine (meth)acrylamindes. Biomacromolecules, 2012, vol. 13, pp. 4146-4170. (Year: 2013).*

Schlenoff, Joseph B. Zwitteration: coating surfaces with zwitterionic functionality to reduce nonspecific adsorption. Langmuir 2014, vol. 30, pp. 9625-9636. (Year: 2014).*

Extended European Search Report dated Mar. 9, 2018 in Patent Application No. 15839337.1, 6 pages.

International Search Report dated Dec. 8, 2015 in PCT/JP2015/075333 filed Sep. 7, 2015.

* cited by examiner

SOLID PHASE CARRIER, LIGAND-BOUND SOLID PHASE CARRIER, METHOD FOR DETECTING OR SEPARATING TARGET SUBSTANCE, AND METHOD FOR PRODUCING SOLID PHASE CARRIER

TECHNICAL FIELD

The present invention relates to a solid phase carrier, a ligand-bound solid phase carrier, a method for detecting or separating a target substance, and a method for producing the solid phase carrier.

BACKGROUND ART

Solid phase carriers have been utilized for the purpose of detecting and separating target substances such as proteins, nucleic acids and cells from samples such as blood. Regarding a method for detection and separation using a solid phase carrier, a method of immobilizing a ligand to a solid phase carrier, bringing a sample into contact with this solid phase carrier, and thereby causing a target substance to react with a ligand, is generally used. However, during the contacting, the target substance or impurities in the sample may non-specifically adsorb not to the ligand but to the surface of the solid phase carrier, and this adsorption may become noises.

Therefore, for the purpose of suppressing the non-specific adsorption, there has been suggested a technology for introducing a certain amount of an atomic transfer radical polymerization initiating group (ATRP initiating group) onto the surface of a gold film chip of a magnetic biosensor, polymerizing a particular carboxybetaine monomer by utilizing such an ATRP initiating group as a starting point, and thereby forming a polymer brush (Patent Literature 1).

However, the gold film chip having the polymer brush makes a ligand to be less likely bound thereto, and capturing of a target substance is achieved insufficiently. Thus, signals of the target substance may not be easily detected.

Meanwhile, in recent years, magnetic particles have been paid attention as a solid phase carrier to be used in, for example, a diagnostic agent for an enzyme immunoassay of clinical examinations, cell separation including cell therapy, and nucleic acid extraction. While magnetic particles are relatively easily separable from, for example, a specimen sample, magnetic particles tend to easily aggregate in water, and thus it is expected to develop a technology for improving water dispersibility of magnetic particles.

Owing to a demand for early diagnosis of diseases or the like, it is also desirable that those magnetic particles used for a diagnostic agent can sufficiently capture a target substance. Furthermore, it is required for those magnetic particles used for cell separation to be able to specifically capture only target cells. Under such circumstances, there have been suggested magnetic particles having a polymer brush formed thereon by bonding, for example, a poly(hydroxyethyl methacrylamide)-poly(methacrylic acid) block copolymer to the surface by ATRP (Patent Literature 2). However, those magnetic particles are susceptible to non-specific adsorption of a target substance or impurities in a sample to the particle surface, and therefore, there is room for improvement from this point of view.

CITATION LIST

Patent Literature

Patent Literature 1: JP 2009-69141 A
Patent Literature 2: JP 2009-542862 W

SUMMARY OF INVENTION

Technical Problem

An object of the present invention is to provide a solid phase carrier which has high water dispersibility, allows facilitated binding of a ligand to a reactive functional group, and exhibits suppressed non-specific adsorption, and with which, in the case of using the solid phase carrier by having a ligand bound thereto, for example, detection of a target substance can be carried out with high sensitivity and low noise.

Solution to Problem

Then, the inventors of the present invention conducted a thorough investigation, and as a result, found that a solid phase carrier having bound thereto a polymer containing a particular structural unit having a zwitterionic structure and a particular structural unit having a reactive functional group, has high water dispersibility, allows facilitated binding of a ligand to the reactive functional group, and exhibits suppressed non-specific adsorption, and with which in case of using the solid phase carrier by having a ligand bound thereto, for example, detection of a target substance can be carried out with high sensitivity and low noise.

That is, the present invention provides <1> a solid phase carrier including a polymer including a structural unit (hereinafter, also referred to as structural unit (1)) represented by the following Formula (1) and a structural unit (hereinafter, also referred to as structural unit (2)) represented by the following Formula (2) bound thereto:

in which in Formula (1),
$R^1$ represents a hydrogen atom or a methyl group; and
$R^2$ represents an organic group having a zwitterionic structure,

in Formula (2),
$R^3$ represents a hydrogen atom or a methyl group;
$R^4$ represents —(C=O)—O—*, —(O=O)—NR$^6$—* (in which $R^6$ represents a hydrogen atom or a methyl group; and the symbol * represents a position of bonding to $R^5$ in Formula (2)), or a phenylene group;
in a case in which $R^4$ represents —(C=O)—O—*, $R^5$ represents a hydrogen atom, or an organic group having a reactive functional group, and in a case in which $R^4$ represents —(C=O)—NR$^6$—* or a phenylene group, $R^5$ represents an organic group having a reactive functional group, provided that $R^5$ is not an organic group having a zwitterionic structure.

Furthermore, the present invention provides <2> a ligand-bound solid phase carrier formed by binding a ligand to the solid phase carrier of <1>.

The present invention also provides <3> a method for detecting or separating a target substance in a sample, the method including using the ligand-bound solid phase carrier of <2>.

The present invention also provides <4> a method for producing a solid phase carrier formed by having bound thereto a polymer containing a structural unit (1) and a structural unit (2), the method including:

(Step 1) a step of preparing a carrier having a polymerization initiating group; and (Step 2) a step of polymerizing a monomer by utilizing the polymerization initiating group as a starting point.

Effects of the Invention

The solid phase carrier of the present invention has high water dispersibility, allows facilitated binding of a ligand to a reactive functional group, and exhibits suppressed non-specific adsorption, and with which in case of using the solid phase carrier by having a ligand bound thereto, for example, detection of a target substance can be carried out with high sensitivity and low noise.

According to the production method of the present invention, the solid phase carrier of the present invention can be conveniently produced.

DETAILED DESCRIPTION OF THE INVENTION

<Solid Phase Carrier>

The solid phase carrier of the present invention is formed by having bound thereto a polymer containing a structural unit represented by the following Formula (1) and a structural unit represented by the following Formula (2). First, the solid phase carrier of the present invention will be described in detail.

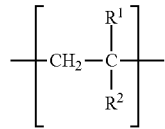
(1)

in which in Formula (1), $R^1$ represents a hydrogen atom or a methyl group; and $R^2$ represents an organic group having a zwitterionic structure.

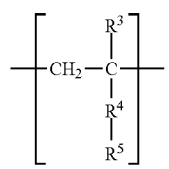
(2)

in which in Formula (2), $R^3$ represent a hydrogen atom or a methyl group;

$R^4$ represents —(C=O)—O—*, —(C=O)—NR$^6$—* (in which $R^6$ represents a hydrogen atom or a methyl group; and the symbol * represents a position that is bonded to $R^5$ in Formula (2)), or a phenylene group;

in a case in which $R^4$ represents —(C=O)—O—*, $R^5$ represents a hydrogen atom, or an organic group having a reactive functional group, and in a case in which $R^4$ represents —(C=O)—NR$^6$—* or a phenylene group, $R^5$ represents an organic group having a reactive functional group;

provided that $R^5$ is not an organic group having a zwitterionic structure.

(Structural Unit (1))

In Formula (1), $R^2$ represents an organic group having a zwitterionic structure. Such an organic group means an organic group having a cationic functional group and an anionic functional group. The organic group having a zwitterionic structure is preferably an organic group having a quaternary ammonium salt type cationic functional group and an anionic functional group, and more preferably an organic group having a quaternary ammonium salt type cationic functional group and a monovalent or divalent anionic functional group selected from the group consisting of —(C=O)O$^-$, —SO$_3^-$ and —O—(O=P—O$^-$)—O—. Among them, regarding $R^2$, an organic group represented by the following Formula (3) or (4) is more preferable from the viewpoint of suppressing non-specific adsorption, and an organic group represented by the following Formula (3) is particularly preferable from the viewpoint that monomer synthesis is feasible.

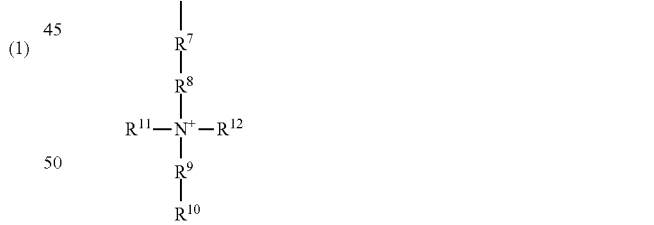
(3)

in which in Formula (3), $R^7$ represents —(C=O)—O—*, —(C=O)—NR$^{13}$—* (in which $R^{13}$ represents a hydrogen atom or a methyl group; and the symbol * represents a position that is bonded to $R^8$ in Formula (3)), or a phenylene group;

$R^8$ and $R^9$ independently represent a single bond or a divalent organic group having 1 to 10 carbon atoms;

$R^{10}$ represents —(C=O)O$^-$ or —SO$_3^-$; and $R^{11}$ and $R^{12}$ independently represent a methyl group or an ethyl group.

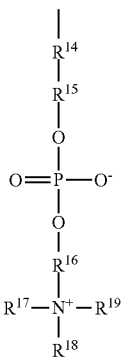

(4)

in which in Formula (4), $R^{14}$ represents =(C=O)—O—*, —(C=O)—NR$^{20}$—* (in which $R^{20}$ represents a hydrogen atom or a methyl group; and the symbol * represents a position that is bonded to $R^{15}$ in Formula (4)), or a phenylene group;

$R^{15}$ and $R^{16}$ independently represent a single bond or a divalent organic group having 1 to 10 carbon atoms; and $R^{17}$, $R^{18}$ and $R^{19}$ independently represent a methyl group or an ethyl group.

In Formula (3), from the viewpoint of increasing the affinity with water and suppressing non-specific adsorption, $R^7$ is preferably —(C=O)—O—* or —(C=O)—NR$^{13}$—*, and more preferably —(C=O)—O—*.

$R^{10}$ represent —(C=O)O$^-$ or —SO$_3^-$; and from the viewpoint of achieving a balance between detection sensitivity enhancement and noise reduction, $R^{10}$ is preferably —(C=O)O$^-$.

$R^{13}$ represents a hydrogen atom or a methyl group, and $R^{13}$ is preferably a hydrogen atom.

$R^8$ and $R^9$ in Formula (3), and $R^{15}$ and $R^{16}$ in Formula (4) independently represent a single bond or a divalent organic group having 1 to 10 carbon atoms. However, from the viewpoint of suppressing non-specific adsorption, a divalent organic group having 1 to 10 carbon atoms is preferred; a divalent hydrocarbon group having 1 to 10 carbon atoms, or a group formed from a divalent hydrocarbon group having 2 to 10 carbon atoms, with one or more selected from the group consisting of an ether bond, an imino group, an amide bond and an ester bond being disposed between carbon-carbon atoms of the divalent hydrocarbon group, is more preferred; and a divalent hydrocarbon group having 1 to 10 carbon atoms is particularly preferred.

In a case in which the divalent organic group is a divalent hydrocarbon group, the number of carbon atoms is preferably 1 to 8, more preferably 1 to 6, even more preferably 1 to 4, and particularly preferably 1 to 3. Meanwhile, in a case in which the divalent organic group is a group formed from a divalent hydrocarbon group, with one or more selected from the group consisting of an ether bond, an imino group, an amide bond and an ester bond being disposed between carbon-carbon atoms of the divalent hydrocarbon group, the number of carbon atoms of the divalent hydrocarbon group in such a group is preferably 2 to 8, more preferably 2 to 6, even more preferably 2 to 4, and particularly preferably 2 or 3.

The "divalent hydrocarbon group" for $R^8$, $R^9$, $R^{15}$ and $R^{16}$ is preferably a divalent aliphatic hydrocarbon group. The divalent aliphatic hydrocarbon group may be a straight chain or a branched chain.

The divalent aliphatic hydrocarbon group is preferably an alkanediyl group, and specific examples include a methane-1,1-diyl group, an ethane-1,1-diyl group, an ethane-1,2-diyl group, a propane-1,1-diyl group, a propane-1,2-diyl group, a propane-1,3-diyl group, a propane-2,2-diyl group, a butane-1,2-diyl group, a butane-1,3-diyl group, a butane-1,4-diyl group, a pentane-1,4-diyl group, a pentane-1,5-diyl group, a hexane-1,5-diyl group, and a hexane-1,6-diyl group.

For $R^{11}$ and $R^{12}$ in Formula (3), and $R^{17}$, $R^{18}$ and $R^{19}$ in Formula (4), a methyl group is preferred.

In Formula (4), from the viewpoint of enhancing the affinity with water and suppressing non-specific adsorption, $R^{14}$ is preferably —(C=O)—O—* or —(C=O)—NR$^{20}$—*, and more preferably —(C=O)—O—*. $R^{20}$ represents a hydrogen atom or a methyl group, and $R^{20}$ is preferably a hydrogen atom.

(Structural Unit (2))

In Formula (2), from the viewpoint of enhancing the affinity with water and suppressing non-specific adsorption, $R^4$ is preferably —(C=O)—O—* or —(C=O)—NR$^6$—*. $R^6$ represents a hydrogen atom or a methyl group, and R is preferably a hydrogen atom.

Furthermore, in a case in which $R^4$ represents —(C=O)—O—*, $R^5$ represents a hydrogen atom, or an organic group having a reactive functional group; and in a case in which $R^4$ represents —(C=O)—NR$^6$—* or a phenylene group, $R^5$ represents an organic group having a reactive functional group. In a case in which $R^4$ is —(C=O)—O—* and $R^5$ is a hydrogen atom, the combination of $R^4$ and $R^5$ becomes a reactive functional group (carboxyl group). However, $R^5$ is not an organic group having a zwitterionic structure represented by $R^2$, and according to the present specification, the reactive functional group in $R^5$ is a concept not containing a zwitterionic structure.

Examples of the reactive functional group include a carboxyl group, a tosyl group, an amino group, an epoxy group, an acyl group, and an azide group, and the aforementioned organic group may have one kind of these, or may have two or more kinds thereof. Among these, from the viewpoint of making the bound ligand not easily detachable, or from the viewpoint that in a case in which a molecule of, for example, a protein or a nucleic acid is used as a ligand, the ligand can be bound to the solid phase carrier using a functional group that the ligand originally contains, a carboxyl group, a tosyl group, an amino group or an epoxy group is preferred, and from the viewpoint that it is easy to have the ligand conveniently and rapidly bound to the solid phase carrier, a carboxyl group is more preferred.

Furthermore, in regard to the content of the reactive functional group contained in the structural unit (2), from the viewpoint of the amount of ligand binding, from the viewpoint of achieving a balance between sensitivity enhancement and noise reduction in detection, or from the viewpoint of the cell separation performance, the content is preferably 1 μmol or more, more preferably 5 μmol or more, even more preferably 10 μmol or more, still more preferably 15 μmol or more, even more preferably 20 μmol or more, still more preferably 25 μmol or more, and particularly preferably 30 μmol or more, per gram of the solid content of the solid phase carrier. Also, from the viewpoint of suppression non-specific adsorption, or from the viewpoint of achieving a balance between sensitivity enhancement and noise reduction in detection, the content is preferably 300 μmol or less, more preferably 200 μmol or less, even more preferably 190 μmol or less, and particularly preferably 180 μmol or less.

The content of the reactive functional group can be measured by an electrical conductivity measuring method, for example, in a case in which the reactive functional group is a carboxyl group, and specifically, the content can be measured according to the method described in the following Examples. Furthermore, in a case in which the reactive functional group is a tosyl group, the content can be determined by, for example, measuring the ultraviolet-visible light absorption of the tosyl group introduced into the solid phase carrier. In a case in which the reactive functional group is an amino group, the content can be determined by, for example, reacting the amino group with N-succinimidyl 3-(2-pyridyldithio)propionate, subsequently reducing the resultant, and measuring the absorbance of free thiopyridyl groups.

Furthermore, the organic group having a reactive functional group represented by $R^5$ is preferably an organic group represented by the following Formula (5).

$$-R^{21}-Y \tag{5}$$

in which in Formula (5), $R^{21}$ represents a divalent organic group; and
Y represents a reactive functional group.

The divalent organic group represented by $R^{21}$ may be a divalent hydrocarbon group, or a group formed from a divalent hydrocarbon group having two or more carbon atoms, with one or more selected from the group consisting of an ether bond, an imino group, an amide bond and an ester bond being disposed between carbon-carbon atoms of the divalent hydrocarbon group.

In a case in which the divalent organic group is a divalent hydrocarbon group, the number of carbon atoms is preferably 1 to 10, more preferably 1 to 8, and particularly preferably 1 to 6. Meanwhile, in a case in which the divalent organic group is a group formed from a divalent hydrocarbon group having 2 or more carbon atoms, with one or more selected from the group consisting of an ether bond, an imino group, an amide bond and an ester bond being disposed between carbon-carbon atoms of the divalent hydrocarbon group, the number of carbon atoms of the divalent hydrocarbon group in such a group is preferably 2 to 10, more preferably 2 to 8, and particularly preferably 2 to 6.

The "divalent hydrocarbon group" for $R^{21}$ is preferably a divalent aliphatic hydrocarbon group. The divalent aliphatic hydrocarbon group may be a straight chain or a branched chain.

The divalent aliphatic hydrocarbon group is preferably an alkanediyl group, and specific examples thereof include a methane-1,1-diyl group, an ethane-1,1-diyl group, an ethane-1,2-diyl group, a propane-1,1-diyl group, a propane-1,2-diyl group, a propane-1,3-diyl group, a propane-2,2-diyl group, a butane-1,2-diyl group, a butane-1,3-diyl group, a butane-1,4-diyl group, a pentane-1,4-diyl group, a pentane-1,5-diyl group, a hexane-1,5-diyl group, and a hexane-1,6-diyl group.

Furthermore, the group formed from a divalent hydrocarbon group having 2 or more carbon atoms, with one or more selected from the group consisting of an ether bond, an imino group, an amide bond and an ester bond being disposed between carbon-carbon atoms of the divalent hydrocarbon group, is preferably a group having an ester bond between carbon-carbon atoms of a divalent hydrocarbon group having 2 or more carbon atoms, and more preferably a divalent group represented by $-R^a-O-(C=O)-R^b-*$ (in which $R^a$ and $R^b$ independently represent an alkanediyl group having 2 to 4 carbon atoms; and the symbol * represents a position of bonding to Y in Formula (5)), from the viewpoint that, for example, a polymer is obtained conveniently. The number of carbon atoms of the alkanediyl group is preferably 2 or 3, and more preferably 2. The alkanediyl group may be a straight chain or a branched chain, and examples thereof include an ethane-1,2-diyl group, a propane-1,2-diyl group, and a propane-1,3-diyl group.

Examples of the reactive functional group represented by Y include, as described above, a carboxyl group, a tosyl group, an amino group, an epoxy group, an acyl group, and an azide group. Among them, from the viewpoint of making the bound ligand not easily detachable, or from the viewpoint that in a case in which a molecule of, for example, a protein or a nucleic acid is used as a ligand, the ligand can be bound to the solid phase carrier using a functional group that the ligand originally contains, a carboxyl group, a tosyl group, an amino group or an epoxy group is preferred, and from the viewpoint that it is easy to have the ligand conveniently and rapidly bound to the solid phase carrier, a carboxyl group is more preferred.

Regarding the combination of $R^4$ and $R^5$ described above, a combination in which $R^4$ is $-(C=O)-O-*$, and $R^5$ is a hydrogen atom or an organic group having a reactive functional group; and a combination in which $R^4$ is $-(C=O)-NR^6-*$, and $R^5$ is an organic group having a reactive functional group are preferred, and a combination in which $R^4$ is $-(C=O)-O-*$ or $-(C=O)-NR^6-*$, and $R^5$ is an organic group having a reactive functional group is more preferred.

Furthermore, the polymer may have a structural unit other than the structural units (1) and (2) (hereinafter, also referred to as other structural unit). Examples of the other structural unit include structural units derived from, for example, (meth)acrylates, styrenes, (meth)acrylonitriles, and vinyl acetate.

The structural units (1) and (2) may be included in the same polymer that is bound to a solid phase carrier, or may be included in different polymers. It is preferable that the structural units (1) and (2) are included in the same polymer.

The average degree of polymerization n of the structural unit (1) per polymer is preferably 1 or higher, more preferably 3 or higher, even more preferably 5 or higher, and particularly preferably 10 or higher. Furthermore, from the viewpoint of the amount of ligand binding, from the viewpoint of achieving a balance between sensitivity enhancement and noise reduction in detection, or from the viewpoint of cell separation performance, the average degree of polymerization n is preferably 500 or lower, more preferably 300 or lower, even more preferably 200 or lower, still more preferably 100 or lower, even more preferably 70 or lower, and particularly preferably 62 or lower.

The average degree of polymerization m of the structural unit (2) per polymer is preferably 1 or higher, more preferably 3 or higher, even more preferably 5 or higher, and particularly preferably 10 or higher, from the viewpoint of the amount of ligand binding. Furthermore, from the viewpoint of suppressing non-specific adsorption, or from the viewpoint of achieving a balance between sensitivity enhancement and noise reduction in detection, the average degree of polymerization m is preferably 500 or lower, more preferably 300 or lower, even more preferably 200 or lower, still more preferably 100 or lower, even more preferably 70 or lower, and particularly preferably 65 or lower.

Furthermore, from the viewpoint of suppressing non-specific adsorption and from the viewpoint of the amount of ligand binding, the proportion of polymerization [m/(m+n)]

calculated from the average degree of polymerization n and the average degree of polymerization m is preferably 0.01 or higher, more preferably 0.03 or higher, even more preferably 0.05 or higher, still more preferably 0.1 or higher, and particularly preferably 0.15 or higher. Furthermore, from the viewpoint of suppressing non-specific adsorption, and from the viewpoint of the amount of ligand binding, the proportion of polymerization is preferably 0.75 or lower, more preferably 0.74 or lower, and particularly preferably 0.7 or lower. In a case in which the polymer is a block polymer, from the viewpoint of suppressing non-specific adsorption, from the viewpoint of the amount of ligand binding, and from the viewpoint of achieving a balance between sensitivity enhancement and noise reduction in detection, particularly making the solid phase carrier adequate for diagnostic agent applications, the proportion of polymerization is even more preferably 0.1 to 0.5, still more preferably 0.1 to 0.35, and particularly preferably 0.15 to 0.3. On the other hand, in a case in which the polymer is a random polymer, from the viewpoint of achieving a balance between sensitivity enhancement and noise reduction in detection, particularly making the solid phase carrier adequate for diagnostic agent applications, the proportion of polymerization is even more preferably 0.2 to 0.7, and particularly preferably 0.35 to 0.7.

The average degrees of polymerization, n and m, mean the average degrees of polymerization of the structural unit (1) and the structural unit (2), respectively, per polymer. The average degrees of polymerization can be determined by X-ray photoelectron spectrophotometry, or can be calculated from, for example, the weight of the polymer bound to 1 g of the solid phase carrier, the molecular weight of the polymer, and the amount of the reactive functional groups. Specifically, the average degrees of polymerization can be measured by the method described in the following Examples.

The polymer is preferably a chain polymer. A chain polymer refers to a polymer having a linear molecular structure, and is a concept including a polymer having a structure including a long straight main chain and relatively short side chains bound thereto.

Also, the polymer is preferably a vinyl polymer. The mode of the arrangement of structural units in the polymer is not particularly limited, and may be any one of a random copolymer, a block copolymer, a copolymer having a random copolymerized unit and a block copolymerized unit, and an alternating copolymer. From the viewpoint that a polymer can be conveniently formed, a random copolymer or a block copolymer is preferred. In a case in which the polymer is a random copolymer, non-specific adsorption of cells for example is easily suppressed. Furthermore, in a case in which the polymer is a block copolymer, ligands, for example, antibodies can be easily bound to the polymer, and a balance between sensitivity enhancement and noise reduction in detection utilizing an antigen-antibody reaction is likely to be achieved. The reasons for obtaining effects as such are not necessarily clearly understood. The inventors of the present invention speculate that it is because in the case of a block copolymer, since the reactive functional groups locally exist, antibodies can be easily bound thereto, and higher-order structures such as a sandwich structure (primary antibody-antigen-secondary antibody) can be easily adopted.

Also, in a case in which the polymer is a block copolymer, this block copolymer is a polymer including containing a first block composed of repeatedly arranged structural units (1), and a second block composed of repeatedly arranged structural units (2). Regarding the block copolymer as such, from the viewpoint of further facilitating binding of a ligand, or from the viewpoint of achieving a balance between sensitivity enhancement and noise reduction in detection, a block copolymer represented by the following Formula (6) is preferred.

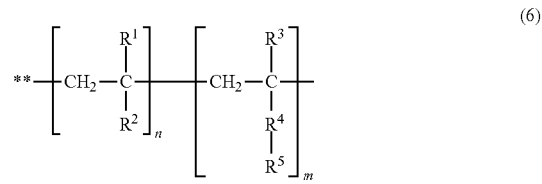

(6)

in which in Formula (6), the symbol ** represents a position of bonding on the solid phase carrier side; and other reference symbols have the same meanings as described above.

Furthermore, one terminal of the polymer is not particularly limited as long as it is bound to the solid phase carrier, and it is preferable that the one terminal is bound to the solid phase carrier via a divalent linking group containing a residue of a polymerization initiating group. Regarding the polymerization initiating group, a polymerization initiating group capable of living polymerization is preferred; a living radical polymerization initiating group is more preferred; an atomic transfer radical polymerization initiating group or a reversible addition fragmentation chain transfer polymerization initiating group is even more preferred; and an atomic transfer radical polymerization initiating group is particularly preferred. The divalent linking group containing a residue of an atomic transfer radical polymerization initiating group may be a divalent group represented by the following Formula (7-1) or (7-2).

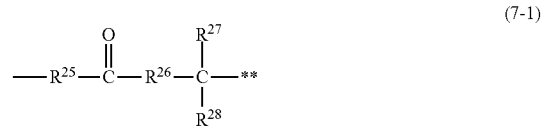

(7-1)

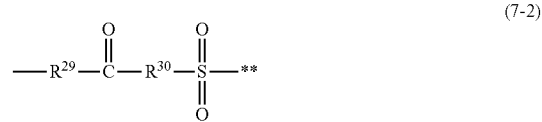

(7-2)

in which $R^{25}$ and $R^{29}$ each represent —O— or —NH—;

$R^{26}$ and $R^{30}$ independently represent a single bond or a phenylene group;

$R^{27}$ and $R^{28}$ independently represent a hydrogen atom or an alkyl group; and the symbol ** represents a position of bonding to a terminal of the polymer.

Regarding $R^{25}$ and $R^{29}$, —O— is preferred; regarding $R^{26}$ and $R^{30}$, a single bond is preferred; and regarding $R^{27}$ and $R^{28}$, an alkyl group is preferred.

The number of carbon atoms of the alkyl group represented by $R^{27}$ and $R^{28}$ is preferably 1 to 8, more preferably 1 to 4, and particularly preferably 1 or 2. The alkyl group may be a straight chain or a branched chain, and specific examples thereof include a methyl group, an ethyl group, a n-propyl group, an isopropyl group, a n-butyl group, an isobutyl group, a sec-butyl group, a tert-butyl group, a pentyl group, a hexyl group, a heptyl group, and an octyl group.

Meanwhile, the other terminal of the polymer is not particularly limited, and a halogen atom is preferred. Examples of the halogen atom include a bromine atom, a chlorine atom, and a fluorine atom.

It is preferable that the polymer forms a polymer brush on the surface of the solid phase carrier. The density of the polymer occupying the surface of the solid phase carrier of the present invention is preferably 0.01 molecules/nm$^2$ or more, more preferably 0.05 molecules/nm$^2$ or more, even more preferably 0.1 molecules/nm$^2$ or more, still more preferably 0.3 molecules/nm$^2$ or more, even more preferably 0.4 molecules/nm$^2$ or more, still more preferably 0.5 molecules/nm$^2$ or more, still more preferably 0.6 molecules/nm$^2$ or more, and particularly preferably 0.7 molecules/nm$^2$ or more, from the viewpoint of suppressing non-specific adsorption, from the viewpoint of the amount of ligand binding, and from the viewpoint of achieving a balance between sensitivity enhancement and noise reduction in detection. Furthermore, from the viewpoint that a polymer brush can be formed conveniently, the density is preferably 2 molecules/nm$^2$ or less, more preferably 1.6 molecules/nm$^2$ or less, and even more preferably 1.2 molecules/nm$^2$ or less.

The density of the polymer can be calculated by, for example, the following formula. Specifically, the polymer is liberated from the solid phase carrier by, for example, hydrolysis, and the density can be measured by the method described in the following Examples.

Density of polymer (molecules/nm$^2$)=Number of polymer molecules bound to 1 g of carrier (molecules)/total surface area of 1 g of carrier (nm$^2$)

Furthermore, the number average molecular weight (Mn) of the polymer is preferably 1,000 to 100,000, more preferably 3,000 to 50,000, and even more preferably 5,000 to 30,000.

The weight average molecular weight (Mw) of the polymer is preferably 1,000 to 100,000, more preferably 3,000 to 50,000, and particularly preferably 5,000 to 30,000.

The molecular weight distribution (Mw/Mn) is preferably 1.0 to 2.5, more preferably 1.0 to 2.0, and even more preferably 1.0 to 1.5, from the viewpoint of suppressing non-specific adsorption and enhancing the activity of the ligand bound to the solid phase carrier.

It is noted that the number average molecular weight and the weight average molecular weight mean average molecular weights determined by liberating the polymer from the solid phase carrier by, for example, hydrolysis, and measuring the molecular weights by gel permeation chromatography, the average molecular weights being calculated in terms of polyethylene glycol standards. The average molecular weights can be calculated by, for example, measuring the molecular weight of the polymer before the introduction of a reactive functional group by a method such as described in the following Examples, and calculating the average molecular weights from such molecular weight, the mole number of the structural unit into which the reactive functional group is to be introduced, and the structure of the compound used for introduction of the reactive functional group.

The constituent other than the polymer, which constitutes the solid phase carrier of the present invention, may be an organic substance or may be an inorganic substance such as a metal or a metal oxide, and it is not particularly limited thereto. It is preferable that the solid phase carrier of the present invention includes a resin other than the polymer.

The resin may be a naturally occurring polymer composed of polysaccharides such as agarose, dextran and cellulose, or may be a synthetic polymer.

The form of the solid phase carrier of the present invention is not particularly limited, and may be any of, for example, particles, a monolith, a film, a fiber, and a chip. From the viewpoint of the ease of detection or separation of a target substance, particles are preferred, and magnetic particles are more preferred.

The term "magnetic particles" according to the present specification means particles having a magnetic body. The solid phase carrier of the present invention has high water dispersibility even if the carrier is in the form of magnetic particles. Furthermore, when the solid phase carrier is produced as magnetic particles, since the solid phase carrier can be separated using, for example, a magnet without using, for example, a centrifuge, separation of the solid phase carrier from a sample can be simplified or automated.

The magnetic body may be any of ferromagnetic, paramagnetic and superparamagnetic; and from the viewpoint of facilitating separation by means of a magnetic field and redispersion after removal of the magnetic field, it is preferable that the magnetic body is superparamagnetic. Examples of the magnetic body include metals or alloys, such as ferrite, iron oxide, iron, manganese oxide, manganese, nickel oxide, nickel, cobalt oxide, and cobalt.

Furthermore, regarding the magnetic particles, specifically particles formed by having the above-described polymer bound to any of the particles of the following items (i) to (iv) may be employed. A preferred example of the magnetic particles is porous or non-porous magnetic polymer particles.

(i) Particles in which magnetic microparticles are dispersed in a continuous phase containing a non-magnetic body such as a resin.

(ii) Particles in which secondary aggregates of magnetic microparticles are constituted as a core, and a non-magnetic body such as a resin is constituted as a shell.

(iii) Particles in which mother particles are formed as cores, the mother particles being have core particles formed from a non-magnetic body such as a resin and a magnetic layer containing magnetic microparticles (secondary aggregate layer) provided on the surface of the core particles; and a non-magnetic layer such as a resin is formed as shell (hereinafter, also referred to as outermost layer shell) on the outermost layer of the mother particles.

(iv) Particles in which magnetic microparticles are dispersed in the pores of porous particles formed from a resin or silica, while the particles may have a non-magnetic layer such as a resin provided as a shell in the outermost layer of the particles.

The particles of (i) to (iv) are all well known, and can be produced according to conventional methods.

An example of the resin for the core particles of (iii) and the porous particles of (iv) may be a resin derived from one kind or two or more kinds selected from the group consisting of monofunctional monomers and crosslinkable monomers.

Examples of the monofunctional monomers include monofunctional aromatic vinyl-based monomers such as styrene, α-methylstyrene, and halogenated styrene; and monofunctional (meth)acrylate-based monomers such as methyl (meth)acrylate, ethyl (meth)acrylate, stearyl (meth)acrylate, cyclohexyl (meth)acrylate, and isobornyl (meth)acrylate.

Examples of the crosslinkable monomers include monofunctional aromatic vinyl-based monomers such as divinylbenzene; polyfunctional (meth)acrylate-based monomers such as ethylene glycol di(meth)acrylate, trimethylolpropane tri(meth)acrylate, dipentaerythritol hexa(meth)acrylate, and allyl (meth)acrylate; and conjugated diolefins such as butadiene and isoprene.

Regarding the resin for use in (i) and (ii) as well as the resin for the outermost layer shell of (iii) and (iv), a resin having one kind or two or more kinds of functional groups selected from the group consisting of a glycidyl group, an amino group and a hydroxyl group is preferred. The functional group may be introduced by chemical modification of the resin, or may be introduced by polymerization of a monomer composition including one kind or two or more kinds of monomers having the aforementioned functional groups. Examples of the chemical modification include production of a hydroxyl group by hydrolysis of a glycidyl group, and production of an amino group by reduction of a nitro group. The monomer composition having the aforementioned functional groups is more preferably a monomer composition including at least a glycidyl group-containing monomer (hereinafter, particles in which the resin in the outermost layer shell is a resin formed from a monomer composition including at least a glycidyl group-containing monomer, are also referred to as glycidyl group-containing magnetic particles). The monomer composition may further include one kind or two or more kinds selected from the group consisting of the monofunctional monomers and crosslinkable monomers described above.

Examples of a glycidyl group-containing monomer include glycidyl (meth)acrylate and ally glycidyl ether. Examples of an amino group-containing monomer include 2-aminoethyl (meth)acrylate. Examples of a hydroxyl group-containing monomer include 1,4-cyclohexanedimethanol mono(meth)acrylate.

The average particle size (volume average particle size) in a case in which the solid phase carrier of the present invention is in a particulate form, is preferably 0.1 to 500 μm, more preferably 0.2 to 50 μm, and even more preferably 0.3 to 10 μm. When the average particle size falls within such a range, in a case in which the solid phase carrier is in the form of magnetic particles, the rate of magnetic collection becomes faster, and handleability is improved. Also, the amount of ligand binding is increased, and satisfactory detection sensitivity is obtained. Furthermore, the coefficient of variation of the average particle size may be about 20% or lower.

Furthermore, the specific surface area may be about 1.0 to 2.0 $m^2/g$.

The average particle size and the specific surface area can be measured by, for example, measuring the laser diffraction/scattering particle size distribution.

<Method for Producing Solid Phase Carrier>

The solid phase carrier of the present invention can be produced by appropriately combining conventional methods; however, regarding the method for producing the solid phase carrier of the present invention, from the viewpoint of increasing the density of the polymer occupying the surface of the solid phase carrier to further suppress non-specific adsorption, from the viewpoint of binding a polymer having a narrow molecular weight distribution to the solid phase carrier to further suppress non-specific adsorption, and from the viewpoint of increasing the function of the ligand to be bound to the solid phase carrier, a method including (Step 1) a step of preparing a carrier having a polymerization initiating group (hereinafter, also referred to as polymerization initiating group-containing carrier); and (Step 2) a step of polymerizing a monomer by utilizing the polymerization initiating group as a starting point, is preferred.

Specific examples of the production method include the following methods <PR-1> and <PR-2>. In the following description, these methods will be described by taking a case in which the reactive functional group included in the structural unit (2) is a carboxyl group, an amino group or a tosyl group, as an example.

<PR-1> A method of (Step 1) preparing a polymerization initiating group-containing carrier; (Step 2-1-1) polymerizing a monomer (11) that constitutes a structural unit (1) and a monomer (12) having a functional group capable of introducing a carboxyl group, an amino group or a tosyl group (for example, a hydroxyl group, an epoxy group, an ester group, an amino group, or a carboxylic acid protective group), by utilizing the polymerization initiating group as a starting point; and (Step 2-1-2) introducing a carboxyl group, an amino group or a tosyl group to the polymer (14) that has been introduced onto the solid phase carrier by an addition reaction, a substitution reaction, a condensation reaction or a deprotection reaction.

<PR-2> A method of (Step 1) preparing a polymerization initiating group-containing carrier; (Step 2-2-1) introducing a carboxyl group, an amino group or a tosyl group into a monomer (12) having a functional group capable of introducing a carboxyl group, an amino group or a tosyl group, by an addition reaction, a substitution reaction, a condensation reaction or a deprotection reaction, and thereby obtaining a monomer (13) that constitutes a structural unit (2); and (Step 2-2-2) polymerizing this monomer (13) with monomer (11) by utilizing the polymerization initiating group as a starting point. When a monomer having a carboxyl group, an amino group or a tosyl group is used, the polymer can be produced without performing (Step 2-2-1). Examples of the monomer having a carboxyl group, an amino group or a tosyl group include (meth)acrylic acid, a (meth)acrylic acid salt, and aminoethyl (meth)acrylate.

(Step 1)

Regarding the polymerization initiating group-containing carrier, a commercially available product may be used, or the carrier may be synthesized for use. For example, the polymerization initiating group-containing carrier can be obtained by bringing a raw material carrier having one kind or two or more kinds selected from the group consisting of a hydroxyl group, an amino group, an epoxy group and a carboxyl group (hereinafter, these may also be collectively referred to as "a hydroxyl group or the like") (hereinafter, also referred to as raw material carrier), into contact with a compound having a polymerization initiating group, and converting the hydrogen atom contained in the hydroxyl group or the like into a polymerization initiating group (hereinafter, this reaction may also be referred to as a polymerization initiating group-introducing reaction). Meanwhile, among the raw material carriers as described above, a raw material carrier having a hydroxyl group can be obtained by, for example, bringing the glycidyl group-containing magnetic particles into contact with an acid such as an inorganic acid or an organic acid, and ring-opening the glycidyl group.

The polymerization initiating group-containing carrier can also be obtained by polymerizing a monomer composition including a monomer having a polymerization initiating group. Examples of the monomer having a polymerization initiating group include 2-(2-bromoisobutyryloxy) ethyl methacrylate.

The compound having a polymerization initiating group is preferably a compound having a polymerization initiating group capable of living polymerization; more preferably a compound having a living radical polymerization initiating group; even more preferably a compound having an atomic transfer radical polymerization initiating group or a compound having a reversible addition fragmentation chain transfer polymerization initiating group; and particularly preferably a compound having an atomic transfer radical polymerization initiating group. Examples of the compound having an atomic transfer radical polymerization initiating group include 2-bromoisobutyryl bromide, 4-(bromomethyl)benzoic acid, ethyl 2-bromoisobutyrate, 2-bromopropionyl bromide, and tosyl chloride.

The total usage amount of the compound having a polymerization initiating group in the polymerization initiating group-introducing reaction is usually about 0.001 to 100 times by mass, and preferably about 0.01 to 50 times by mass, with respect to the raw material carrier.

The polymerization initiating group-introducing reaction is preferably performed in the presence of a basic catalyst such as triethylamine, N,N-dimethyl-4-aminopyridine, diisopropylethylamine, or pyridine. These basic catalysts may be used singly, or in combination of two or more kinds thereof.

The total usage amount of the basic catalyst is usually about 1 to 10 molar equivalents, and preferably about 1 to 5 molar equivalents, with respect to the compound having a polymerization initiating group.

Furthermore, the polymerization initiating group-introducing reaction is preferably performed in the presence of a solvent. Examples of the solvent include ether-based solvents such as tetrahydrofuran, 1,4-dioxane, and 1,3-dioxane; and protic solvents such as dimethylformamide and dimethyl sulfoxide. These solvents may be used singly or in combination of two or more kinds thereof.

The reaction time for the polymerization initiating group-introducing reaction is usually about 30 minutes to 24 hours, and the reaction temperature may be appropriately selected to be lower than or equal to the boiling point of the solvent.

(Step 2-1-1)

The polymerization method for the polymerization reaction in Step 2-1-1 may be selected depending on the type of the polymerization initiating group. However, from the viewpoint of obtaining an intended substance conveniently and easily, living polymerization is preferred; living radical polymerization is more preferred; atomic transfer radical polymerization (ATRP polymerization) or reversible addition fragmentation chain transfer polymerization (RAFT polymerization) is even more preferred; and atomic transfer radical polymerization is particularly preferred. By polymerizing the polymer by atomic transfer radical polymerization, the polymer can be conveniently bound to a wide variety of carriers, and biocompatibility, high compressive elasticity, low friction characteristics, and size exclusion characteristics are imparted to the resulting solid phase carrier. Also, since the density of polymer occupying the surface of the solid phase carrier is increased, non-specific adsorption does not easily occur.

In addition, a block copolymer can be introduced into a solid phase carrier by polymerizing the monomer (12), after having the monomer (11) polymerized, by utilizing the polymerization initiating group at a terminal of the polymer thus formed, as a starting point; or by polymerizing the monomer (11), after having the monomer (12) polymerized, by utilizing the polymerization initiating group at a terminal of the polymer thus formed, as a starting point.

Examples of the monomer (11) include [2-((meth)acryloyloxy)ethyl] (carboxylatomethyl)dimethylaminium, [2-((meth)acryloyloxy)ethyl] (carboxylatoethyl)dimethylaminium, [2-((meth)acryloyloxy)ethyl] (carboxylatopropyl) dimethylaminium, [2-((meth)acryloyloxy)ethyl]dimethyl-(3-sulfomethyl)ammonium hydroxide, [2-((meth)acryloyloxy)ethyl]dimethyl-(3-sulfoethyl)ammonium hydroxide, [2-((meth)acryloyloxy)ethyl]dimethyl-(3-sulfopropyl)ammonium hydroxide, and O-[2-((meth)acryloyloxy)ethoxy(oxylato)phosphinyl]choline. Among these, one kind thereof may be used alone, or two or more kinds thereof may be used in combination.

Examples of the monomer (12) include 2-hydroxyethyl (meth)acrylamide, 2-hydroxyethyl (meth)acrylate, glycidyl (meth)acrylate, aminoethyl (meth)acrylate, and tert-butyl (meth)acrylate. Among these, one kind thereof may be used alone, or two or more kinds thereof may be used in combination.

The total amounts of use of the monomers (11) and (12) are each usually about 5 to 10,000 molar equivalents, and preferably about 10 to 5,000 molar equivalents, with respect to the respective polymerization initiating groups bound to the carrier.

In a case in which the polymerization reaction in Step 2-1-1 is performed by atomic transfer radical polymerization, from the viewpoint of the reaction efficiency, it is preferable to perform the reaction in the presence of a transition metal compound and a ligand.

The transition metal compound is preferably a copper compound. Examples of the copper compound include copper halides such as copper(I) bromide, copper(II) bromide, copper(I) chloride, and copper(II) chloride; copper(I) triflate and copper(II) triflate. Among these, one kind thereof may be used alone, or two or more kinds thereof may be used in combination. The total usage amount of the transition metal compound is usually about 1 to 10,000 ppm in the reaction system.

The ligand is preferably a ligand containing two or more nitrogen atoms in the same molecule. Examples of the ligand containing two or more nitrogen atoms in the same molecule include tris(2-pyridylmethyl)amine, bipyridine, bipyridine derivatives, and tris[2-(dimethylamino)ethyl]amine. Among these, one kind thereof may be used alone, or two or more kinds thereof may be used in combination. The total usage amount of the ligand is usually about 0.5 to 10 molar equivalents with respect to the transition metal compound.

From the viewpoint of the reaction efficiency, it is preferable that the polymerization reaction in Step 2-1-1 is performed in the presence of a reducing agent and a solvent.

Examples of the reducing agent include ascorbic acid, glucose, hydrazine, and copper, and these reducing agents can be used singly or in combination of two or more kinds thereof.

Examples of the solvent include water; amide-based solvents such as dimethylformamide; and alcohol-based solvents such as methanol and ethanol. These solvents can be used singly or in combination of two or more kinds thereof in combination.

The pH of the reaction system of the polymerization reaction is preferably 3 to 10. The reaction time for the polymerization reaction is usually about 30 minutes to 12 hours, and the reaction temperature may be appropriately selected to be lower than or equal to the boiling point of the solvent. The polymerization reaction proceeds also under mild conditions of about 25° C. to 60° C.

(Step 2-1-2)

Step 2-1-2 is a step of introducing a carboxyl group, an amino group or a tosyl group to the polymer (14) that has been introduced into the solid phase carrier, by means of an addition reaction, a substitution reaction, a condensation reaction, or a deprotection reaction.

Examples of the method for introducing a carboxyl group include a method of using a monomer having a hydroxyl group or an amino group as the monomer (12), and subjecting the polymer (14) thus obtained to an addition reaction with a carboxylic acid anhydride; a method of using a monomer having an epoxy group as the monomer (12), hydrolyzing the polymer (14) thus obtained to produce a hydroxyl group, and then subjecting the polymer (14) to an addition reaction with a carboxylic acid anhydride; a method of using a monomer having an epoxy group as the monomer (12), and subjecting the polymer (14) thus obtained to an addition reaction with a compound having a nucleophilic group such as a mercapto group or an amino group and a carboxyl group; and a method of using a monomer having a protected carboxyl group as the monomer (12), and deprotecting the polymer (14) thus obtained.

Examples of the carboxylic acid anhydride include succinic anhydride, maleic anhydride, glutaric anhydride, phthalic anhydride, and hexahydrophthalic anhydride. Among them, from the viewpoint that the reaction with a hydroxyl group or an amino group readily proceeds, succinic anhydride is preferred. The total usage amount of, for example, carboxylic acid anhydride is usually about 0.1 to 2,000 molar equivalents, and preferably 1 to 1,000 molar equivalents, with respect to the structural unit derived from the monomer (12).

Examples of the compound having a nucleophilic group such as a mercapto group or an amino group and a carboxyl group include mercaptopropionic acid and an amino acid. Examples of the monomer having a protected carboxyl group include tert-butyl (meth)acrylate and N-hydroxysuccinimide (meth)acrylate. Meanwhile, the deprotection method can be carried out by a well-known method depending on the protected group, and examples thereof include hydrolysis.

Examples of the method for introducing an amino group include a method of using a monomer having an epoxy group as the monomer (12), and subjecting the polymer (14) thus obtained to an addition reaction with ammonia or a compound having two or more amino groups. Examples of the compound having two or more amino groups include ethylenediamine.

Examples of the method for introducing a tosyl group include a method of using a monomer having a hydroxyl group or an amino group as the monomer (12), and adding tosyl chloride to the polymer (14) thus obtained; and a method of using a monomer having an epoxy group as the monomer (12), hydrolyzing the polymer (14) thus obtained to produce a hydroxyl group, and then adding tosyl chloride thereto.

It is also preferable that Step 2-1-2 is carried out in the presence of a basic catalyst and a solvent similar to those used in Step 1. The reaction time for Step 2-1-2 is usually about 30 minutes to 24 hours, and the reaction temperature may be appropriately selected to be lower than or equal to the boiling point of the solvent.

Meanwhile, Step 2-2-1 may be carried out equivalently to Step 2-1-2, and Step 2-2-2 may be carried out equivalently to Step 2-1-1.

The solid phase carrier of the present invention obtainable as described above has high water dispersibility, allows facilitated binding of a ligand to a reactive functional group, and exhibits suppressed non-specific adsorption. Furthermore, in a case in which the solid phase carrier is used by having a ligand bound thereto, the S/N (signal/noise) ratio in, for example, the detection of a target substance can be increased, and for example, detection can be carried out with high sensitivity and reduced noise. Also, separation of a target substance can be achieved with high purity. In a case in which the solid phase carrier is used by having a ligand bound thereto, target cells can be specifically captured at a high rate.

Therefore, when the solid phase carrier of the present invention is used as an affinity carrier, the solid phase carrier can be widely utilized in studies in extracorporeal diagnoses and in the field of biochemistry, including immunoassays utilizing an antigen-antibody reaction, such as an enzyme immunoassay, a radioimmunoassay, and a chemiluminescence immunoassay; detection of proteins and nucleic acids; bioseparation of bio-related materials such as cells, proteins, and nucleic acids; drug seeking; and biosensors. The solid phase carrier of the present invention is especially suitable for an immunoassay, for bioseparation (particularly cell separation), and for use intended for nucleic acid detection.

<Ligand-Bound Solid Phase Carrier>

The ligand-bound solid phase carrier of the present invention is formed by binding a ligand to the solid phase carrier of the present invention.

The ligand is desirably a molecule that binds to a target substance, and examples thereof include antibodies; antigens; nucleic acids such as DNA and RNA; nucleotides; nucleosides; proteins such as Protein A, Protein G, (strept) avidin, enzymes, and lectin; peptides such as insulin; amino acids; sugars or polysaccharides, such as heparin; lipids; vitamins such as biotin; drugs; substrates; hormones; neurotransmitters; and synthetic molecules.

Among these, from the viewpoint of making a ligand-bound solid phase carrier appropriate for use in, for example, diagnostic agents, the ligand is preferably an antibody or an antigen. The antibody and the antigen may be any antibody or antigen that binds to a target substance, and examples thereof include antibodies for solidification fibrinolysis-related to examination, such as anti-Antiplasmin antibody, anti-D dimer antibody, anti-FDP antibody, anti-tPA antibody, anti-Thrombin-antithrombin complex antibody and anti-FPA antibody, or antigens to these; antibodies for tumor-related tests, such as anti-BFP antibody, anti-CEA antibody, anti-AFP antibody, anti-TSH antibody, anti-Ferritin antibody, anti-CA19-9 antibody, or antigens to these; antibodies for serum protein-related tests, such as anti-Apolipoprotein antibody, anti-$\beta$2-microblobulin antibody, anti-$\alpha$1-microglobulin antibody, anti-Immunoglobulin antibody, anti-CRP antibody and anti-EpCAM antibody, or antigens to these; antibodies for endocrine function tests, such as anti-HCG antibody, or antigens to these; antibodies for drug analysis, such as anti-Digoxin antibody and anti-Lidocaine antibody, or antigens to these; antigens for infection-related tests, such as HBs antigen, HCV antigen, HIV-1 antigen, HIV-2 antigen, HTLV-1 antigen, *mycoplasma* antigen, *toxoplasma* antigen and streptolysin O antigen, or antibodies to these; and antigens for autoimmunity-related tests, such as DNA antigen and thermally modified human IgG, or antibodies to these. The antibodies may be polyclonal antibodies or may be monoclonal antibodies.

Binding of the ligand may be carried out according to a conventional method; however, it is preferable that binding is carried out by a covalent binding method. For example, in a case in which the reactive functional group is a carboxyl group, and the ligand has an amino group, binding may be achieved using a dehydration condensation agent.

The ligand-bound solid phase carrier of the present invention can be widely utilized in, for example, extracorporeal diagnoses and studies in the field of biochemistry. The ligand-bound solid phase carrier of the present invention is especially suitable for an immunoassay, for bioseparation (particularly cell separation), and for use in nucleic acid detection.

<Method for Detecting or Separating Target Substance>

The method for detecting or separating a target substance in a sample of the present invention uses the ligand-bound solid phase carrier of the present invention.

The target substance may be any substance capable of binding to the ligand, and specific examples include antigens; antibodies such as monoclonal antibodies and polyclonal antibodies; cells (normal cells, and cancer cells such as large intestine cancer cells and blood-circulating cancer cells); nucleic acids such as DNA and RNA; and bio-related substances such as proteins, peptides, amino acids, sugars, polysaccharides, lipids, and vitamins. The target substance may also be a drug that serves as a potential drug target, or a small molecular weight compound such as biotin. Meanwhile, the target substance may be a substance that has been labeled with, for example, a fluorescent substance.

The sample may be any sample which includes the target substance, or which has a possibility of including a target substance. Specific examples include blood, blood plasma, blood serum, and a buffer solution containing a target substance.

The method for detection or separation of the present invention may be carried out according to a conventional method, except that the ligand-bound solid phase carrier of the present invention is used. For example, the method may be a method including a step of bringing the ligand-bound solid phase carrier of the present invention into contact with a target substance by, for example, mixing (contacting step); and a step of separating the ligand-bound solid phase carrier that has captured the target substance, from the sample using, for example, a magnet (separation step). The method may further include, after the separation step, a step of detecting the target substance, or a step of dissociating the ligand and the target substance.

EXAMPLES

Hereinafter, the present invention will be described in detail by way of Examples; however, the present invention is not intended to be limited to these Examples. The various analysis conditions for the Examples are described below.

<Measurement of Molecular Weight of Chain Polymer>

The molecular weight of the chain polymer was measured after the chain polymer was liberated from the particles by performing hydrolysis using an aqueous solution of sodium hydroxide.

That is, 1 g of particles were dispersed in 4 g of an aqueous solution of sodium hydroxide (1 N, pH 14), the dispersion was stirred for 3 hours at 25° C., and thereby a chain polymer was liberated from the particles. The particles were separated using magnetism, and a supernatant having the chain polymer dissolved therein was collected. Next, 1 M hydrochloric acid was added to this chain polymer solution until the pH of the solution reached 7, and thus the solution was neutralized. In order to make use for the calculation of the weight of the chain polymer, the weight of sodium chloride produced from the weight of 1 M hydrochloric acid added thereto was calculated, and the solution after neutralization was freeze-dried. Thereby, a chain polymer including sodium chloride was obtained as a powder. Furthermore, the weight of the powder was measured in order to use the weight for the calculation of the weight of the chain polymer.

The powder was used as a specimen, and Mn and Mw of the chain polymer formed on the particle surface were measured by making measurement by gel permeation chromatography (GPC) under the following conditions, using a TSKgel G3000PWXL column manufactured by Tosoh Corp. and Chrom NAV chromatography data station program manufactured by JASCO Corp.

(Measurement Conditions)

Flow rate: 0.8 mL/min

Elution solvent: 0.2 M sodium phosphate buffer solution (pH 7.0)

Column temperature: 25° C.

Standard substance: TSKgel standard Poly(ethylene oxide) SE-kit manufactured by Tosoh Corp., and Polyethylene Glycol 4,000 manufactured by Wako Pure Chemical Industries, Ltd.

<Polymer Density of Chain Polymer Occupying Particle Surface>

The polymer density was calculated by the following formula, from the weight of the chain polymer liberated from the particles, the number average molecular weight of the chain polymer, and the surface area of the particles.

[Density of chain polymer occupying particle surface (chains/nm$^2$)]=[Number of chain polymer molecules bonded to 1 g of particles (chains)]/[total surface area per gram of particles (nm$^2$)]

The calculation methods for the number of chain polymer molecules bonded to 1 g of particles and the total surface area of 1 g of the particles are as follows.

(Number of Chain Polymer Molecules Bonded to 1 g of Particles)

The weight of the chain polymer bonded to 1 g of particles was calculated by the following formula ($\alpha$), and from the value thus obtained, the number of the chain polymer molecules bonded to 1 g of the particles was calculated by the following formulae ($\beta$) and ($\gamma$).

Weight (mg) of chain polymer bonded to 1 g of particles=Weight (mg) of powder after being freeze-dried−weight (mg) of sodium chloride ($\alpha$):

Number (mol) of chain polymer molecules bonded to 1 g of particles={Weight (mg) of chain polymer bonded to 1 g of particles÷number average molecular weight (g/mol) of chain polymer}÷1000 ($\beta$):

Number (chains) of chain polymer molecules bonded to 1 g of particles=Number (mol) of chain polymer molecules bonded to 1 g of particles×6.02× 10$^{23}$ (Avogadro's number) ($\gamma$):

(Total Surface Area Per Gram of Particles)

The total surface area per gram of particles was calculated by the following formulae ($\delta$) to ($\theta$). The specific gravity of particles in formula ($\epsilon$) was calculated from the specific gravity of the polymer, the specific gravity of the magnetic body, and the ratio of the polymer and the magnetic body.

Volume (μm$^3$) per particle=4/3×π×{volume average radius (μm) of particles}$^3$ ($\delta$):

Mass per particle (g)=Volume (μm$^3$) per particle× specific gravity of particles (g/μm$^3$) ($\epsilon$):

Number of particles (particles) per gram of particles=1 g/mass per particle (g) ($\zeta$):

Surface area (nm$^2$) per particle=4×π×{radius (nm) of particle}$^2$   (η):

Total surface area (nm$^2$) per gram of particles=Surface area (nm$^2$) per particle×number of particles (particles) per gram of particles   (θ):

<Content of Reactive Functional Group>

The content of the reactive functional group (carboxyl group) contained in the chain polymer liberated from the particles was measured using an electrical conductivity measurement method (Metrohm A G, 794 Basic Titrino), and thereby the content of the reactive functional groups per gram of the solid content of the particles was determined.

<Proportion of Polymerization [m/(m+n)]>

The value of m/(m+n) was calculated from the average degree of polymerization n obtainable from the following formulae (A), (B) and (C), and the average degree of polymerization m obtainable from the following formula (D).

Weight (g) of structural unit (2) per gram of particles=Amount (mol) of reactive functional groups per gram of particles×molecular weight (g/mol) of structural unit (2)   (A):

Weight (g) of structural unit (1) per gram of particles=Weight (g) of chain polymer per gram of particles−weight (g) of structural unit (2) per gram of particles   (B):

n={Weight (g) of structural unit (1) per gram of particles/molecular weight (g/mol) of structural unit (1)}/number of polymer molecules (molecules) per gram of particles   (C):

m=Amount of reactive functional groups (mol) per gram of particles/number of polymer molecules (molecules) per gram of particles   (D):

<Volume Average Particle Size>

The volume average particle sizes of various particles were measured using a laser diffraction/scattering particle size distribution analyzer (Beckman Coulter LS13 320).

Synthesis Example 1 Synthesis of Magnetic Particles Having Hydroxyl Groups on Surface 2 g of a 75% solution of di(3,5,5-trimethylhexanoyl) peroxide ("PEROYL 355-75(S)", manufactured by NOF Corp.) was mixed with 20 g of a 1 mass % aqueous solution of sodium dodecyl sulfate, and the mixture was finely emulsified with an ultrasonic disperser. This was introduced into a reactor containing 13 g of polystyrene particles (number average particle size: 0.77 μm) and 41 g of water, and the mixture was stirred for 12 hours at 25° C.

Next, in another vessel, 96 g of styrene and 4 g of divinylbenzene were emulsified with 400 g of a 0.1 mass % aqueous solution of sodium dodecyl sulfate, and this was introduced into the reactor and stirred for 2 hours at 40° C. Subsequently, the temperature was elevated to 75° C., and polymerization was performed for 8 hours. The system was cooled to room temperature, and then only particles were taken out by centrifugation and were washed with water and dried. These particles are designated as core particles (number average particle size: 1.5 μm).

Next, in another separate vessel, acetone was added to an oily magnetic fluid ("EXP series, EMG", manufactured by Ferrotec Corporation), and particles were precipitated and settled. Subsequently, the particles were dried, and thereby ferrite-based magnetic microparticles (average primary particle size: 0.01 μm) having a hydrophobized surface were obtained.

Next, 15 g of the core particles and 15 g of the hydrophobized magnetic microparticles were thoroughly mixed with a mixer, and this mixture was treated for 5 minutes using a hybridization system NHS-O type (manufactured by Nara Machinery Co., Ltd.) at a circumferential speed of the blade (stirring blade) of 100 m/second (16,200 rpm). Thus, mother particles having on the surface a magnetic layer formed from magnetic microparticles (number average particle size: 2.0 μm) were obtained.

Next, 250 g of a 0.50 mass % aqueous solution of sodium dodecyl sulfate was introduced into a 500-mL separable flask, and then 10 g of the mother particles having a magnetic layer were added thereto. The mixture was dispersed with a homogenizer, and then was heated to 60° C. The dispersion was maintained at that temperature.

Next, 75 g of a 0.50 mass % aqueous solution of sodium dodecyl sulfate, 13.5 g of methyl methacrylate (hereinafter, referred to as "MMA"), 1.5 g of trimethylolpropane trimethacrylate (hereinafter, referred to as "TMP"), and 0.3 g of a 75% solution of di(3,5,5-trimethylhexanoyl) peroxide ("PEROYL 355-75(S)", manufactured by NOF Corp.) were introduced into another vessel, and the mixture was dispersed to obtain a pre-emulsion. The whole amount of this pre-emulsion was added dropwise for 2 hours to the 500-mL separable flask that had been maintained at 60° C. After completion of the dropwise addition, the mixture was stirred for one hour while being maintained at 60° C.

37.5 g of a 0.50 mass % aqueous solution of sodium dodecyl sulfate, 6.56 g of glycidyl methacrylate (hereinafter, referred to as "GMA"), 0.94 g of TMP, and 0.15 g of a 75% solution of di(3,5,5-trimethylhexanoyl) peroxide ("PEROYL 355-75(S)", manufactured by NOF Corp.) were introduced into another vessel, and the mixture was dispersed. Thus, a pre-emulsion was obtained. The whole amount of this pre-emulsion was added dropwise for 1 hour and 20 minutes to the 500-mL separable flask that had been maintained at 60° C. Subsequently, the mixture was heated to 75° C., and then polymerization was continued for 2 hours. Then, the reaction was completed. Subsequently, 10 mL of a 1 mol/L aqueous solution of sulfuric acid was introduced into this 500-mL separable flask, and the mixture was stirred for 6 hours at 60° C. Next, particles in the 500-mL separable flask were separated using magnetism, and then the particles were repeatedly washed with distilled water.

Thus, magnetic particles having hydroxyl groups on the surface were obtained.

Synthesis Example 2 Synthesis of Magnetic Particles Having Atomic Transfer Radical Polymerization Initiating Groups on Surface (1)

10 g of the magnetic particles having hydroxyl groups on the surface, which were obtained in Synthesis Example 1, were introduced into a flask, and under nitrogen flow, 32 mL of dehydrated tetrahydrofuran and 7.5 mL of triethylamine were added thereto. The mixture was stirred. This flask was immersed in an ice bath, and 6.3 mL of 2-bromoisobutyryl bromide was added dropwise thereto for 30 minutes. The mixture was allowed to react for 6 hours at room temperature, subsequently the particles in the flask were separated using magnetism, and then the particles were subjected to a redispersion in acetone. Magnetic separation and redispersion were further performed several times, and then the particles were dispersed in a 0.10 mass % aqueous solution of sodium dodecyl sulfate. Br contained in the atomic transfer radical polymerization initiating group (2-bromoisobutyryl group) was detected by a fluorescent X-ray analysis.

Thus, magnetic particles having atomic transfer radical polymerization initiating groups (2-bromoisobutyryl groups) on the surface were obtained. These particles are designated as particles (A).

Synthesis Example 3 Synthesis of Magnetic Particles Having Atomic Transfer Radical Polymerization Initiating Groups (2)

10 g of magnetic particles having hydroxyl groups on the surface, which were obtained in Synthesis Example 1, were introduced into a flask, and under nitrogen flow, 32 mL of dehydrated tetrahydrofuran and 0.4 mL of triethylamine were added thereto. The mixture was stirred. This flask was immersed in an ice bath, and 0.2 mL of 2-bromoisobutyryl bromide was added. The mixture was allowed to react for 6 hours at room temperature, subsequently particles in the flask were separated using magnetism, and then the particles were subjected to a redispersion in acetone. Magnetic separation and redispersion were further performed several times, and then the particles were dispersed in a 0.10 mass % aqueous solution of sodium dodecyl sulfate. Br contained in the atomic transfer radical polymerization initiating group (2-bromoisobutyryl group) was detected by a fluorescent X-ray analysis.

Thus, magnetic particles having atomic transfer radical polymerization initiating groups (2-bromoisobutyryl groups) on the surface were obtained. These particles were designated as particles (B).

Synthesis Example 4 Synthesis of Magnetic Particles Having Atomic Transfer Radical Polymerization Initiating Groups (3)

10 g of magnetic particles having hydroxyl groups on the surface, which were obtained in Synthesis Example 1, were introduced into a flask, and under nitrogen flow, 32 mL of dehydrated tetrahydrofuran and 0.2 mL of triethylamine were added thereto. The mixture was stirred. This flask was immersed in an ice bath, and 0.1 mL of 2-bromoisobutyryl bromide was added dropwise thereto for 30 minutes. The mixture was allowed to react for 6 hours at room temperature, subsequently the particles in the flask were separated using magnetism, and then the particles were subjected to a redispersion in acetone. Magnetic separation and redispersion were further performed several times, and then the particles were dispersed in a 0.10 mass % aqueous solution of sodium dodecyl sulfate. Br contained in the atomic transfer radical polymerization initiating group (2-bromoisobutyryl group) was detected by a fluorescent X-ray analysis.

Thus, magnetic particles having atomic transfer radical polymerization initiating groups (2-bromoisobutyryl groups) on the surface were obtained. These particles are designated as particles (C).

Example 1

(Chain Polymer Extension Reaction (1))

A chain polymer extension reaction was performed according to the following synthesis procedure.

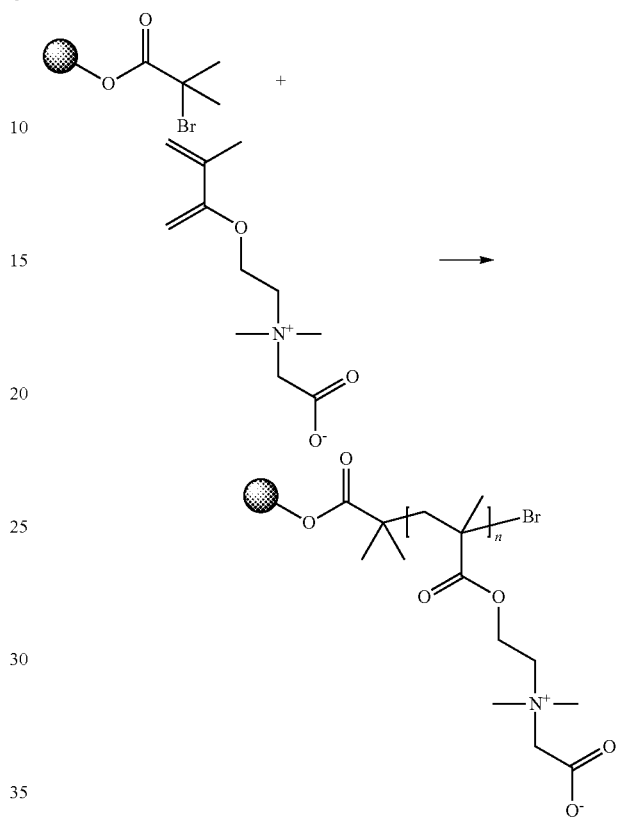

That is, 2 g of the particles (A) obtained in Synthesis Example 2 were dispersed in 6 mL of a sodium phosphate buffer solution (50 mM, pH 7.8), and to this, 0.5 g of [2-(methacryloyloxy)ethyl] (carboxylatomethyl)dimethylaminium (hereinafter, referred to as "CBMA") and 0.40 mL of a mixed aqueous solution of 0.05 mol/L of tris(2-pyridylmethyl)amine and 0.05 mol/L of copper(II) bromide were added. Subsequently, 1.0 mL of a 0.2 mol/L aqueous solution of L-ascorbic acid was added thereto, the mixture was tightly sealed, and a reaction was initiated. The system was stirred for 4 hours at 45° C., and then the reaction was stopped by opening the seal and exposing the system to air. The particles were separated using magnetism, and for example, any unreacted monomers or catalyst was removed.

(Chain Polymer Extension Reaction (2))

Next, a chain polymer extension reaction was performed according to the following synthesis procedure.

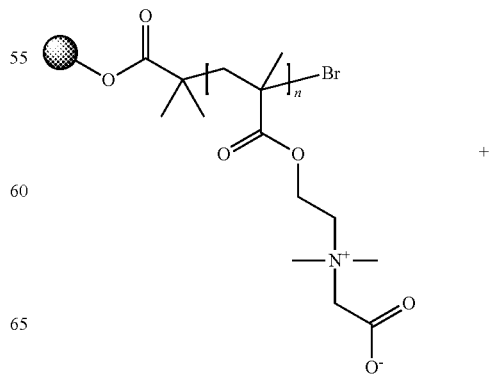

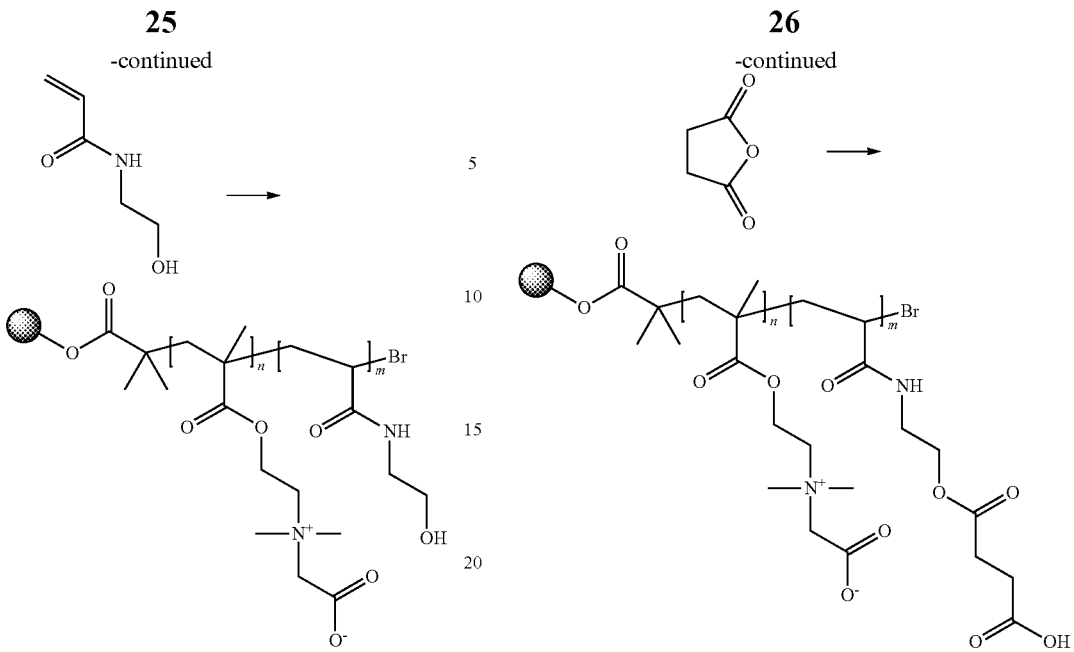

That is, the particles obtained as described above were dispersed in 6 mL of a sodium phosphate buffer solution (50 mM, pH 7.8), and to this, 0.5 g of 2-hydroxyethylacrylamide (hereinafter, referred to as "HEAA") and 0.40 mL of a mixed aqueous solution of 0.05 mol/L of tris(2-pyridylmethyl) amine and 0.05 mol/L of copper (II) bromide were added. Subsequently, 1.0 mL of a 0.2 mol/L aqueous solution of L-ascorbic acid was added thereto, the mixture was tightly sealed, and a reaction was initiated. The system was stirred for 3 hours at 45° C., and then the reaction was stopped by opening the seal and exposing the system to air. The particles were separated using magnetism, and for example, any unreacted monomers or catalyst was removed. Thereby, magnetic particles having a block copolymer of CBMA and HEAA bonded to the surface were obtained. The volume average particle size was 3.0 µm. The Mn, Mw, and Mw/Mn of the block copolymer of CBMA and HEAA, and the polymer density of the block copolymer were measured. The measurement results are presented in Table 1.

(Condensation reaction) Next, a condensation reaction was performed according to the following synthesis procedure.

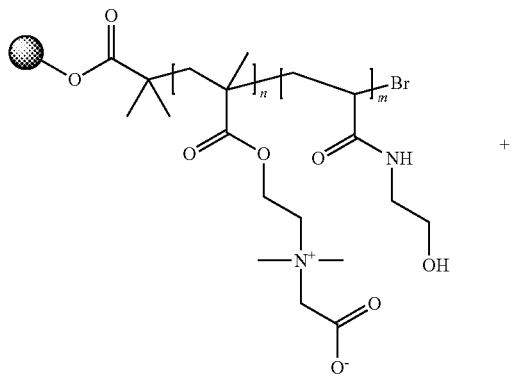

That is, 1.5 g of the particles obtained as described above were dispersed in 8 mL of dimethyl sulfoxide (DMSO), and to this, 7.2 mL of a DMSO solution having 1.5 g of succinic anhydride dissolved therein, and 0.3 mL of triethylamine were added. Thus, a reaction was initiated. The system was stirred for 4 hours at 25° C., subsequently the particles were separated using magnetism, and any excess raw materials were removed.

Thus, Magnetic Particles 1 on which the terminal hydroxyl groups of HEAA had been converted to reactive functional groups (carboxyl groups) were obtained. The content of carboxyl groups and the proportion of polymerization [m/(m+n)] were measured. The measurement results are presented in Table 1.

Example 2

The operation was carried out in the same manner as in Example 1, except that the reaction time for the chain polymer extension reaction (2), by which the chain polymer was extended with HEAA, was changed from 3 hours to 1 hour. Thus, Magnetic Particles 2 on which the terminal hydroxyl groups of HEAA had been converted to reactive functional groups (carboxyl groups) were obtained. The volume average particle size was 3.0 µm.

Various measurement results obtained in the same manner as in Example 1, except for the volume average particle size, are presented in Table 1.

Example 3

The operation was carried out in the same manner as in Example 1, except that the reaction time for the chain polymer extension reaction (2), by which the chain polymer was extended with HEAA, was changed from 3 hours to 30 minutes. Thus, Magnetic Particles 3 on which the terminal hydroxyl groups of HEAA had been converted to reactive functional groups (carboxyl groups) were obtained. The volume average particle size was 3.0 m.

Various measurement results obtained in the same manner as in Example 1, except for the volume average particle size, are presented in Table 1.

Example 4

The operation was carried out in the same manner as in Example 1, except that the reaction time for the chain polymer extension reaction (2), by which the chain polymer was extended with HEAA, was changed from 3 hours to 15 minutes. Thus, Magnetic Particles 4 on which the terminal hydroxyl groups of HEAA had been converted to reactive functional groups (carboxyl groups) were obtained. The volume average particle size was 3.0 µm.

Various measurement results obtained in the same manner as in Example 1, except for the volume average particle size, are presented in Table 1.

Example 5

2 g of the particles (A) obtained in Synthesis Example 2 were dispersed in 6 mL of a sodium phosphate buffer solution (50 mM, pH 7.8), and to this, 0.5 g of CBMA, 0.5 g of HEAA, and 0.40 mL of a mixed aqueous solution of 0.05 mol/L of tris(2-pyridylmethyl)amine and 0.05 mol/L of copper(II) bromide were added. Subsequently, 1.0 mL of a 0.2 mol/L aqueous solution of L-ascorbic acid was added thereto, the mixture was tightly sealed, and a reaction was initiated. The system was stirred for 4 hours at 45° C., and then the reaction was stopped by opening the seal and exposing the system to air. The particles were separated using magnetism, and for example, any unreacted monomers or catalyst was removed. Thus, magnetic particles having a random copolymer of CBMA and HEAA bonded to the surface were obtained. The Mn, Mw, and Mw/Mn of the random copolymer of CBMA and HEAA, and the polymer density of the random copolymer were measured. The measurement results are presented in Table 1.

1.5 g of the particles obtained as described above were dispersed in 8 mL of dimethyl sulfoxide (DMSO), and to this, 7.2 mL of a DMSO solution having 1.5 g of succinic anhydride dissolved therein, and 0.3 mL of triethylamine were added. Thus, a reaction was initiated. The system was stirred for 4 hours at 25° C., subsequently the particles were separated using magnetism, and any excess raw materials were removed.

Thus, Magnetic Particles 5 on which the terminal hydroxyl groups of HEAA had been converted to reactive functional groups (carboxyl groups) were obtained. The volume average particle size was 3.0 µm. The content of carboxyl groups and the proportion of polymerization [m/(m+n)] were measured. The measurement results are presented in Table 1.

Example 6

The operation was carried out in the same manner as in Example 5, except that the usage amount of CBMA was changed from 0.5 g to 0.8 g, and the usage amount of HEAA was changed from 0.5 g to 0.2 g. Thus, Magnetic Particles 6 on which the terminal hydroxyl groups of HEAA had been converted to reactive functional groups (carboxyl groups) were obtained. The volume average particle size was 3.0 µm.

The measurement results obtained in the same manner as in Example 5, except for the volume average particle size, are presented in Table 1.

Example 7

The operation was carried out in the same manner as in Example 2, except that the particles (A) were changed to the particles (B) obtained in Synthesis Example 3, and thus Magnetic Particles 7 on which the terminal hydroxyl groups of HEAA had been converted to reactive functional groups (carboxyl groups) were obtained. The volume average particle size was 3.0 µm.

The measurement results obtained in the same manner as in Example 1, except for the volume average particle size, are presented in Table 1.

Example 8

(Chain Like Polymer Chain Extension Reaction (1))

2 g of the particles (A) obtained in Synthesis Example 2 were dispersed in 6 mL of a sodium phosphate buffer solution (50 mM, pH 7.8), and to this, 0.5 g of 2-(methacryloyloxy)ethyl]dimethyl-(3-sulfopropyl)ammonium hydroxide (hereinafter, referred to as "SBMA"), and 0.40 mL of a mixed aqueous solution of 0.05 mol/L of tris(2-pyridylmethyl)amine and 0.05 mol/L of copper(II) bromide were added. Subsequently, 1.0 mL of a 0.2 mol/L aqueous solution of L-ascorbic acid was added thereto, the mixture was tightly sealed, and a reaction was initiated. The system was stirred for 4 hours at 45° C., and then the reaction was stopped by opening the seal and exposing the system to air. The particles were separated using magnetism, and for example, any unreacted monomers or catalyst was removed.

(Chain Like Polymer Extension Reaction (2))

Next, the particles obtained as described above were dispersed in 6 mL of a sodium phosphate buffer solution (50 mM, pH 7.8), and to this, 0.5 g of HEAA, and 0.40 mL of a mixed aqueous solution of 0.05 mol/L of tris(2-pyridylmethyl)amine and 0.05 mol/L of copper(II) bromide were added. Subsequently, 1.0 mL of a 0.2 mol/L aqueous solution of L-ascorbic acid was added thereto, the mixture was tightly sealed, and a reaction was initiated. The system was stirred for 30 minutes at 45° C., and then the reaction was stopped by opening the seal and exposing the system to air. The particles were separated using magnetism, and for example, any unreacted monomers or catalyst was removed. Thus, magnetic particles having a block copolymer of SBMA and HEAA bonded to the surface were obtained. The volume average particle size was 3.0 m. The Mn, Mw, and Mw/Mn of the block copolymer of SBMA and HEAA, and the polymer density of the block copolymer were measured. The measurement results are presented in Table 1.

(Condensation Reaction)

Next, 1.5 g of the particles obtained as described above were dispersed in 8 mL of dimethyl sulfoxide (DMSO), and to this, 7.2 mL of a DMSO solution having 1.5 g of succinic anhydride dissolved therein, and 0.3 mL of triethylamine were added. Thus, a reaction was initiated. The system was stirred for 4 hours at 25° C., subsequently the particles were separated using magnetism, and any excess raw materials were removed.

Thus, Magnetic Particles 8 on which the terminal hydroxyl groups of HEAA had been converted to reactive functional groups (carboxyl groups) were obtained. The content of carboxyl groups and the proportion of polymerization [m/(m+n)] were measured. The measurement results are presented in Table 1.

Comparative Example 1

2 g of the particles (A) obtained in Synthesis Example 2 were dispersed in 6 mL of a sodium phosphate buffer solution (50 mM, pH 7.8), and to this, 0.5 g of 2-hydroxyethyl methacrylate (hereinafter, referred to as "HEMA"), and 0.40 mL of a mixed aqueous solution of 0.05 mol/L of tris(2-pyridylmethyl)amine and 0.05 mol/L of copper(II) bromide were added. Subsequently, 1.0 mL of a 0.2 mol/L aqueous solution of L-ascorbic acid was added thereto, the mixture was tightly sealed, and a reaction was initiated. The system was stirred for 4 hours at 45° C., and then the reaction was stopped by opening the seal and exposing the system to air. The particles were separated using magnetism, and for example, any unreacted monomers or catalyst was removed. Thus, Magnetic Particles 9 having a homopolymer of HEMA bonded to the surface were obtained. The volume average particle size was 3.0 µm.

Comparative Example 2

The operation was carried out in the same manner as in Example 2, except that CBMA was changed to dimethylaminoethyl methacrylate quaternization product (LIGHT ESTER DQ-100 manufactured by Kyoeisha Chemical Co., Ltd. (product obtained by quaternizing dimethylaminoethyl methacrylate with methyl chloride)). Thus, Magnetic Particles 10 on which the terminal hydroxyl groups of HEAA had been converted to reactive functional groups (carboxyl groups) were obtained. The volume average particle size was 3.0 µm.

The measurement results obtained in the same manner as in Example 1, except for the volume average particle size, are presented in Table 1.

Comparative Example 3

The operation was carried out in the same manner as in Example 6, except that CBMA was changed to dimethylaminoethyl methacrylate quaternization product (LIGHT ESTER DQ-100 manufactured by Kyoeisha Chemical Co., Ltd. (product obtained by quaternizing dimethylaminoethyl methacrylate with methyl chloride)). Thus, Magnetic Particles 11 on which the terminal hydroxyl groups of HEAA had been converted to reactive functional groups (carboxyl groups) were obtained. The volume average particle size was 3.0 m.

The measurement results obtained in the same manner as in Example 5, except for the volume average particle size, are presented in Table 1.

Comparative Example 4

1 g of the magnetic particles having hydroxyl groups on the surface, which were obtained in Synthesis Example 1, were dispersed in 4.8 mL of 1,3-dioxolane, and to this, a solution obtained by dissolving 0.2 mL of triethylamine and 0.08 g of succinic anhydride in 4.8 mL of 1,3-dioxolane was added. A reaction was performed for 4 hours at 25° C., and then the particles were separated using magnetism, and the particles were dispersed in water. Thus, reactive functional group-containing Magnetic Particles 12 that did not have any chain polymer were obtained. The content of carboxyl groups was measured. The measurement results are presented in Table 1.

Comparative Example 5

2 g of the particles (A) obtained in Synthesis Example 2 were dispersed in 6 mL of a sodium phosphate buffer solution (50 mM, pH 7.8), and to this, 0.5 g of CBMA, and 0.40 mL of a mixed aqueous solution of 0.05 mol/L of tris(2-pyridylmethyl)amine and 0.05 mol/L of copper(II) bromide were added. Subsequently, 1.0 mL of a 0.2 mol/L aqueous solution of L-ascorbic acid was added thereto, the mixture was tightly sealed, and a reaction was initiated. The system was stirred for 4 hours at 45° C., and then the reaction was stopped by opening the seal and exposing the system to air. The particles were separated using magnetism, and for example, any unreacted monomers or catalyst was removed. Thus, Magnetic Particles 13 having a homopolymer of CBMA bonded to the surface were obtained. The volume average particle size was 3.0 µm.

Test Example 1 (Water Dispersibility)

100 mg of the magnetic particles obtained in various Examples and Comparative Examples were respectively dispersed in 1 mL of water. The magnetic particles obtained in Comparative Example 1 exhibited poor dispersibility in water, and the particles aggregated. Other magnetic particles were dispersed without aggregating. The evaluation results are presented in Table 2.

Test Example 2 (Non-Specific Adsorption Suppressing Effect)

1 mg of the magnetic particles obtained in each of Examples and Comparative Examples 2 to 5 were dispersed in 2 mL of water. This water dispersion liquid was introduced into an Eppendorf tube, the particles were separated using magnetism, and a supernatant was removed therefrom. Next, 100 µL of a Jurkat disrupted cell suspension (including 100 µg of protein impurities) was added to the particles, the mixture was incubated for 30 minutes, and then the particles were separated using magnetism. A supernatant was removed, and the particles were washed five times with TBS-T (0.05 mass % Tween 20) buffer solution. The particles were separated again using magnetism, a supernatant was removed, and then an aqueous solution of sodium dodecyl benzenesulfonate (0.5 mass %) was added to the particles to detach non-specifically adsorbed protein impurities from the particles. This detachment solution was subjected to SDS-polyacrylamide gel electrophoresis, and the gel was subjected to CBB staining. The amount of proteins that had non-specifically adsorbed to the particles was visually checked, and the non-specific adsorption was evaluated in accordance with the following criteria. As the particles have a smaller amount of proteins, the particles are satisfactory particles having less non-specific adsorption. The evaluation results are presented in Table 2.
(Evaluation Criteria)
  4: Adsorption of proteins is hardly observed, and the state is very good.
  3: Adsorption of proteins is not much observed, and the state is good.
  2: Adsorption of proteins is slightly observed, and the state is somewhat good.
  1: Adsorption of proteins is clearly recognized, and the state is poor.

Test Example 3 (Amount of Antibody Binding)

1 mg of the magnetic particles obtained in each of Examples and Comparative Examples 2 to 5 were dispersed in 2 mL of water. This water dispersion liquid was introduced into an Eppendorf tube, the particles were separated using magnetism, and a supernatant was removed. Next, the particles were dispersed in 990 µL of a MES buffer solution (100 mM, pH 5.0), 10 µL of 1-ethyl-3-(3-dimethylaminopropyl)carbodiimide hydrochloride (10 mg/mL) was added thereto, and the mixture was incubated for 30 minutes at room temperature. The particles were separated using magnetism, and a supernatant was removed. The particles were dispersed in 1 mL of a MES buffer solution (100 mM, pH 5.0), and 15 μg of anti-TSH antibody (manufactured by Funakoshi Co., Ltd.) was added thereto. The mixture was incubated for 12 hours at room temperature, subsequently the particles were separated using magnetism, and a supernatant was removed. The particles were washed five times with a TBS-T (0.05 mass % Tween 20) buffer solution, and thus antibody-bound particles were obtained.

Next, the amount of antibody binding was determined by a BCA assay. That is, 1 mg of the antibody-bound particles were dispersed in 1 mL of an A/B mixed solution of BCA Protein Assay Reagent Kit (manufactured by Thermo Fisher Scientific, Inc.), and the dispersion was subjected to an inversion mixing for 30 minutes at 37° C. The particles were separated using magnetism, a supernatant was removed, and the absorbance at 570 nm was measured. Separately, antibody solutions prepared by dissolving 0 μg, 2 μg, 4 μg, 8 μg, and 16 μg of anti-TSH antibody were respectively mixed with 1 mL of the A/B mixed solution, and the mixtures were subjected to an inversion mixing for 30 minutes at 37° C. Subsequently, the absorbances of the reaction solutions at 570 nm were measured. The amount of antibody binding bound to the magnetic particles was determined from a calibration curve thus obtained. The results are presented in Table 2.

Test Example 4 (CLEIA)

5 μL of a dispersion liquid of the antibody-bound particles obtained in Test Example 3 (equivalent to 50 μg of the particles) was introduced into a test tube, and this was mixed with 50 μL of a 200 μIU/mL TSH antigen solution (LUMIPULSE TSH-III standard TSH solution manufactured by Fujirebio, Inc.) containing 50 μL of fetal calf serum (FCS). The mixture was allowed to react for 10 minutes at 25° C. The particles were separated using magnetism, and a supernatant was removed. Subsequently, 40 μL of anti-TSH antibody labeled with alkali phosphatase (included in LUMIPULSE TSH-III immunoreaction cartridge manufactured by Fujirebio, Inc.) was added as a secondary antibody to the particles. The mixture was allowed to react for 10 minutes at 25° C. The particles were separated using magnetism, a supernatant was removed, and then the particles were repeatedly washed three times with PBS. The particles thus obtained were dispersed in 50 μL of 0.01% Triton X-100, and the dispersion was transferred to a new tube. 100 μL of a substrate solution for alkali phosphatase (LUMIPULSE substrate solution manufactured by Fujirebio, Inc.) was added thereto, the mixture was allowed to react for 10 minutes at 37° C., and then the amount of chemiluminescence was measured as a signal. For the measurement of chemiluminescence, a chemiluminescence analyzer (LUMAT LB9507) manufactured by Berthold Japan Co., Ltd. was used. The amount of chemiluminescence as noise was measured in the same manner as described above, except that 0 μIU/mL of TSH calibrator was used instead of the 200 μIU/mL TSH antigen solution. Furthermore, the value determined by dividing the signal (S) by the noise (N), S/N, was calculated. The results are presented in Table 2.

Test Example 5 (Cell Capture Rate)

1 mg of the magnetic particles obtained in each of Examples and Comparative Examples 2 to 5 were dispersed in 2 mL of water. This water dispersion liquid was introduced into an Eppendorf tube, the particles were separated using magnetism, and a supernatant was removed. Next, the particles were dispersed in 990 μL of a MES buffer solution (100 mM, pH 5.0), 10 μL of 1-ethyl-3-(3-dimethylaminopropyl)carbodiimide hydrochloride (10 mg/mL) was added thereto, and the mixture was incubated for 30 minutes at room temperature. The particles were separated using magnetism, and a supernatant was removed. The particles were dispersed in 1 mL of a MES buffer solution (100 mM, pH 5.0), and 5 μg of anti-EpCAM antibody was added thereto. The mixture was incubated for 12 hours at room temperature, subsequently the particles were separated using magnetism, and a supernatant was removed. The particles were washed five times with a TBS-T (0.05 mass % Tween 20) buffer solution, and thus antibody-bound particles were obtained.

These antibody-bound particles were washed four times with a PBS (−) buffer solution, and then the particles were dispersed in 250 μL of a PBS (−) buffer solution. Next, 90,000 large intestine cancer cells (HT-29) dispersed in 50 μL of Dulbecco's PBS (−) buffer solution were mixed with the antibody-bound particles, the mixture was stirred for 30 minutes at 4° C., and cell capturing was implemented. The particles were separated using magnetism, and a supernatant was removed. The particles were washed four times with a PBS (−) buffer solution, and thereby cell-captured particles were obtained. Next, 50 μL of Proteinase K was added to the cell-captured particles, and the mixture was allowed to react for 15 minutes at 55° C. and then for 20 minutes at 100° C. Thus, the DNA contained in the cells was eluted. The particles were separated using magnetism, a supernatant was collected, and then PCR was performed by adding a PCR cocktail targeting β-globin. The specific cell capture rate was calculated from the number of captured cells that was determined from the Ct value. The results are presented in Table 2.

The operation was carried out in the same manner as described above, except that EpCAM antibody was not bound to the particles, and the non-specific cell capture rate was calculated from the number of captured cells. The results are presented in Table 2.

TABLE 1

|  |  | n | m | m/(m + n) | Polymer density (molecules/nm$^2$) | Mn | Mw | Mw/Mn | Amount of reactive functional groups (μmol/g) | Polymer shape |
|---|---|---|---|---|---|---|---|---|---|---|
| Example | 1 | 59 | 70 | 0.54 | 1.0 | 20,100 | 24,100 | 1.2 | 200 | Block polymer |
|  | 2 | 61 | 23 | 0.28 | 1.0 | 15,000 | 16,500 | 1.1 | 66 | Block polymer |
|  | 3 | 58 | 14 | 0.19 | 1.0 | 13,300 | 16,000 | 1.2 | 39 | Block polymer |
|  | 4 | 57 | 7 | 0.11 | 1.0 | 12,300 | 14,800 | 1.2 | 20 | Block polymer |

TABLE 1-continued

|  |  | n | m | m/(m + n) | Polymer density (molecules/nm²) | Mn | Mw | Mw/Mn | Amount of reactive functional groups (µmol/g) | Polymer shape |
|---|---|---|---|---|---|---|---|---|---|---|
|  | 5 | 36 | 62 | 0.63 | 1.0 | 14,500 | 16,000 | 1.1 | 178 | Random polymer |
|  | 6 | 76 | 23 | 0.23 | 1.0 | 18,100 | 21,700 | 1.2 | 65 | Random polymer |
|  | 7 | 64 | 33 | 0.34 | 0.3 | 16,800 | 21,800 | 1.3 | 28 | Block polymer |
|  | 8 | 55 | 15 | 0.21 | 1.1 | 20,700 | 22,800 | 1.1 | 42 | Block polymer |
| Comparative Example | 1 | — | — | — | — | — | — | — | — | Homopolymer |
|  | 2 | 67*¹ | 23 | 0.25 | 1.0 | 16,600 | 19,900 | 1.2 | 65 | Block polymer |
|  | 3 | 79*¹ | 21 | 0.24 | 1.0 | 18,800 | 22,600 | 1.2 | 60 | Random polymer |
|  | 4 | — | — | — | — | — | — | — | 10 | — |
|  | 5 | 100 | 0 | 0 | 1.0 | 10,200 | 11,200 | 1.1 | 0 | Homopolymer |

*¹ Degree of polymerization of structural unit derived from dimethylaminoethyl methacrylate quaternization product

TABLE 2

|  |  | Water dispersibility | Non-specific adsorption suppressing effect | Amount of antibody binding (µg/mg beads) | CLEIA Signal | CLEIA Noise | CLEIA S/N | Specific cell capture rate (%) | Non-specific cell capture rate (%) |
|---|---|---|---|---|---|---|---|---|---|
| Example | 1 | ○ | 2 | 12 | 83,654 | 198 | 422 | 83 | 3 |
|  | 2 | ○ | 3 | 12 | 147,855 | 157 | 942 | 81 | 2 |
|  | 3 | ○ | 3 | 10 | 148,369 | 179 | 829 | 80 | 2 |
|  | 4 | ○ | 4 | 6 | 94,238 | 140 | 673 | 85 | 1 |
|  | 5 | ○ | 4 | 9 | 125,224 | 152 | 824 | 82 | 1 |
|  | 6 | ○ | 4 | 6 | 82,379 | 140 | 588 | 79 | 1 |
|  | 7 | ○ | 3 | 5 | 91,202 | 195 | 468 | 76 | 5 |
|  | 8 | ○ | 3 | 10 | 130,843 | 165 | 793 | 80 | 2 |
| Comparative Example | 1 | X (Aggregated) | — | — | — | — | — | — | — |
|  | 2 | ○ | 1 | 8 | 108,738 | 435 | 250 | 62 | 24 |
|  | 3 | ○ | 1 | 6 | 74,673 | 378 | 198 | 63 | 21 |
|  | 4 | ○ | 1 | 5 | 94,634 | 215 | 440 | 60 | 45 |
|  | 5 | ○ | 4 | 1 | 3,789 | 140 | 27 | 1 | 1 |

As shown in Tables 1 and 2, the magnetic particles of Examples 1 to 8 exhibited high water dispersibility and suppressed non-specific adsorption, and allowed facilitated binding of ligands to reactive functional groups. Furthermore, the magnetic particles exhibited high S/N (signal/noise) ratios, and could detect antigens with high sensitivity and reduced noise. The magnetic particles of Examples 1 to 8 could specifically capture target cells with at a high proportion, and could suppress non-specific adsorption.

The invention claimed is:

1. A solid phase carrier, comprising a polymer comprising a structural unit represented by Formula (1) and a structural unit represented by Formula (2) bound thereto:

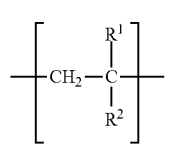
(1)

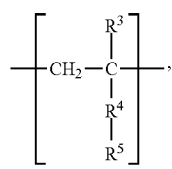
(2)

wherein:

$R^1$ represents a hydrogen atom or a methyl group;

$R^2$ represents an organic group represented by Formula (3);

$R^3$ represents a hydrogen atom or a methyl group;

$R^4$ represents —(C=O)—O—*, —(C=O)—NR⁶—* or a phenylene group;

$R^5$ represents an organic group represented by Formula (5), provided that $R^5$ is not an organic group having a zwitterionic structure;

$R^6$ represents a hydrogen atom or a methyl group; and the symbol * represents a position of bonding to $R^5$ in Formula (2);

(3)

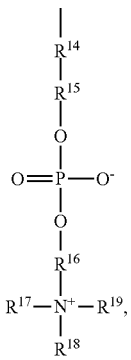

wherein:
$R^7$ represents —(C=O)—O—*, —(C=O)—NR$^{13}$—* or a phenylene group;
$R^{13}$ represents a hydrogen atom or a methyl group;
the symbol * represents a position of bonding to $R^8$ in Formula (3);
$R^8$ and $R^9$ independently represent a divalent organic group having 1 to 10 carbon atoms;
$R^{10}$ represents —(C=O)O; and
$R^{11}$ and $R^{12}$ independently represent a methyl group or an ethyl group;

$$R^{21}—Y \tag{5}$$

wherein:
$R^{21}$ represents a divalent organic group having two or more carbon atoms and one or more selected from the group consisting of an ether bond, an imino group, an amide bond and an ester bond being disposed between carbon-carbon atoms of the divalent hydrocarbon group; and
Y represents a reactive functional group,
wherein the reactive functional group is a carboxyl group, a tosyl group, an amino group, or an epoxy group;
wherein the solid phase carrier is in the form of magnetic particle.

2. The solid phase carrier according to claim 1, wherein the density of the polymer occupying the surface of the solid phase carrier is 0.1 to 1.2 molecules/nm$^2$.

3. The solid phase carrier according to claim 1, wherein the weight average molecular weight of the polymer is 1,000 to 100,000.

4. The solid phase carrier according to claim 1, wherein the molecular weight distribution of the polymer is 1.0 to 2.5.

5. The solid phase carrier according to claim 1, wherein an average degree of polymerization n of the structural unit represented by Formula (1), and an average degree of polymerization m of the structural unit represented by Formula (2) are 1 or larger, respectively, and a proportion of polymerization [m/(m+n)] is 0.01 to 0.75.

6. The solid phase carrier according to claim 1, wherein the polymer is a block polymer comprising a first block comprising repeatedly arranged structural units represented by Formula (1), and a second block comprising repeatedly arranged structural units represented by Formula (2).

7. The solid phase carrier according to claim 1, wherein the polymer is a random polymer.

8. The solid phase carrier according to claim 1, wherein a content of the reactive functional group is 1 to 190 μmol per gram of the solid content of the solid phase carrier.

9. The solid phase carrier according to claim 1, obtained by a method comprising:
polymerizing a monomer capable of forming the structural unit represented by Formula (1) with a monomer capable of forming the structural unit represented by Formula (2) by utilizing a carrier having a polymerization initiating group, said the polymerization initiating group serving as a starting point of polymerization.

10. The solid phase carrier according to claim 9, wherein the polymerization initiating group is an atomic transfer radical polymerization initiating group.

11. A ligand-bound solid phase carrier, comprising
the solid phase carrier of claim 1; and
a ligand bound thereto.

12. The ligand-bound solid phase carrier according to claim 11, wherein the ligand is selected from the group consisting of an antibody, an antigen, a nucleic acid, a nucleotide, a nucleoside, a protein, a peptide, an amino acid, a polysaccharide, a sugar, a lipid, a vitamin, a drug, a substrate, a hormone, a neurotransmitter, and a synthetic molecule.

13. The solid phase carrier of claim 1, which is adapted to function as a solid phase carrier for an immunoassay, a cell separation, or a nucleic acid detection.

14. A method for detecting or separating a target substance in a sample, the method comprising contacting the ligand-bound solid phase carrier of claim 11 with a target substance; wherein said ligand is capable of specifically binding to said target substance.

15. A method for producing a solid phase carrier, the solid phase carrier having bound thereto a polymer comprising a structural unit represented by Formula (1) and a structural unit represented by Formula (2):

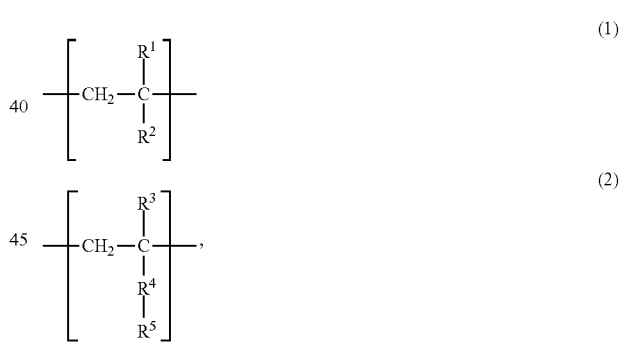

the method comprising
polymerizing a monomer capable of forming the structural unit represented by Formula (1) with a monomer capable of forming the structural unit represented by Formula (2) by utilizing a carrier having a polymerization initiating group, said polymerization initiating group serving as a starting point of polymerization:
wherein:
$R^1$ represents a hydrogen atom or a methyl group;
$R^2$ represents an organic group represented by Formula (3);
$R^3$ represents a hydrogen atom or a methyl group;
$R^4$ represents —(C=O)—O—*, —(C=O)—NR$^6$—* or a phenylene group;
$R^5$ represents an organic group represented by Formula (5), provided that $R^5$ is not an organic group having a zwitterionic structure;

$R^6$ represents a hydrogen atom or a methyl group; and the symbol * represents a position of bonding to $R^5$ in Formula (2);

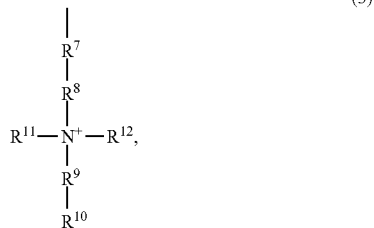
(3)

the symbol * represents a position of bonding to $R^8$ in Formula (3);

$R^8$ and $R^9$ independently represent a divalent organic group having 1 to 10 carbon atoms;

$R^{10}$ represents —(C=O)O; and $R^{11}$ and $R^{12}$ independently represent a methyl group or an ethyl group;

(5)

wherein:

$R^{21}$ represents a divalent organic group having two or more carbon atoms and one or more selected from the group consisting of an ether bond, an imino group, an amide bond and an ester bond being disposed between carbon-carbon atoms of the divalent hydrocarbon group; and Y represents a reactive functional group, wherein the reactive functional group is a carboxyl group, a tosyl group, an amino group, or an epoxy group;

wherein the solid phase carrier is in the form of magnetic particle.

16. The solid phase carrier according to claim 1, wherein the average degree of polymerization n of the structural unit represented by Formula (1), and the average degree of polymerization m of the structural unit represented by Formula (2) are 1 or larger, respectively, and the proportion of polymerization [m/(m+n)] is 0.01 to 0.34.

17. The solid phase carrier according to claim 1, wherein the reactive functional group is a carboxyl group.

18. The method for producing a solid phase carrier according to claim 15, wherein the polymerization initiating group is an atomic transfer radical polymerization initiating group.

19. The solid phase carrier according to claim 1, wherein an average particle size of the magnetic particles is 0.1 to 50 µm.

20. The method for producing a solid phase carrier according to claim 15, wherein an average particle size of the magnetic particles is 0.1 to 50 µm.

21. The solid phase carrier according to claim 1, wherein the polymer does not comprise a structural unit derived from styrene, and one terminal of the polymer is bound to the solid phase carrier via a divalent group represented by Formula (7-1) or (7-2):

(7-1)

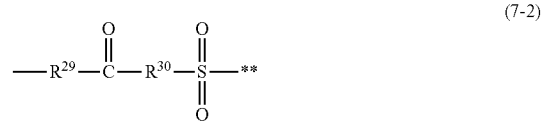
(7-2)

wherein $R^{25}$ and $R^{29}$ each represent —O— or —NH—;

$R^{26}$ and $R^{30}$ independently represent a single bond or a phenylene group;

$R^{27}$ and $R^{28}$ independently represent a hydrogen atom or an alkyl group; and the symbol ** represents a position of bonding to the one terminal of the polymer.

22. The solid phase carrier according to claim 1, wherein $R^{21}$ is represented by —$R^a$—O(C=O)—$R^b$—*, wherein $R^a$ and $R^b$ each independently represent an alkanediyl group having 2 to 4 carbon atoms; and the symbol * represents a position of bonding to Y in Formula (5).

23. The solid phase carrier according to claim 22, wherein the alkanediyl group has 2 to 3 carbon atoms.

* * * * *